US009809595B2

(12) United States Patent
Samatey et al.

(10) Patent No.: US 9,809,595 B2
(45) Date of Patent: Nov. 7, 2017

(54) FLAGELLAR AND NEEDLE COMPLEX (INJECTOSOME) LOOP AS ANTI BACTERIAL DRUG TARGET

(71) Applicant: OKINAWA INSTITUTE OF SCIENCE AND TECHNOLOGY SCHOOL CORPORATION, Kunigami-gun, Okinawa (JP)

(72) Inventors: Fadel Alexis Samatey, Kunigami-gun (JP); Vladimir A Meshcheryakov, Kunigami-gun (JP); Hideyuki Matsunami, Kunigami-gun (JP); Akio Kitao, Tokyo (JP)

(73) Assignee: OKINAWA INSTITUTE OF SCIENCE AND TECHNOLOGY SCHOOL CORPORATION, Okinawa (JP)

(*) Notice: Subject to any disclaimer, the term of this patent is extended or adjusted under 35 U.S.C. 154(b) by 0 days.

(21) Appl. No.: 14/770,708

(22) PCT Filed: Feb. 27, 2014

(86) PCT No.: PCT/JP2014/056082
§ 371 (c)(1),
(2) Date: Aug. 26, 2015

(87) PCT Pub. No.: WO2014/133197
PCT Pub. Date: Sep. 4, 2014

(65) Prior Publication Data
US 2016/0002239 A1    Jan. 7, 2016

Related U.S. Application Data

(60) Provisional application No. 61/770,046, filed on Feb. 27, 2013.

(51) Int. Cl.
| | | |
|---|---|---|
| *C07D 473/08* | (2006.01) | |
| *A61K 31/505* | (2006.01) | |
| *A61K 31/522* | (2006.01) | |
| *C12Q 1/02* | (2006.01) | |
| *C12Q 1/18* | (2006.01) | |
| *C07D 239/49* | (2006.01) | |

(52) U.S. Cl.
CPC .......... *C07D 473/08* (2013.01); *A61K 31/505* (2013.01); *A61K 31/522* (2013.01); *C07D 239/49* (2013.01); *C12Q 1/025* (2013.01); *C12Q 1/18* (2013.01); *G01N 2333/255* (2013.01); *G01N 2500/04* (2013.01)

(58) Field of Classification Search
None
See application file for complete search history.

(56) References Cited

FOREIGN PATENT DOCUMENTS

WO    WO 2010/118046 A1    10/2010

OTHER PUBLICATIONS

Houppert et al., "Identification of Chromosomal Genes in Yersinia pestis that Influence Type III Secretion and Delivery of Yops into Target Cells", PLoS ONE, vol. 7, Issue 3, e34039, Mar. 2012, pp. 1-13.
International Search Report issued in PCT/JP2014/056082, dated Jun. 10, 2014.
Mizuno et al., "The NMR Structure of FliK, the Trigger for the Switch of Substrate Specificity in the Flagellar Type III Secretion Apparatus", Journal of Molecular Biology, vol. 409, No. 4, , 2011 p. 558-573.
Pan et al., "Targeting Type III Secretion in Yersinia pestis", Antimicrobial Agents and Chemotherapy, vol. 53, No. 2, Feb. 2009, pp. 385-392.
Riordan et al; "YscU cleavage and the assembly of Yersinia type III secretion machine complexes", Molecular Microbiology, vol. 68, No. 6, 2008, pp. 1485-1501.
Tsou et al., "Small molecules aimed at type III secretion systems to inhibit bacterial virulence", Med. Chem. Commun., vol. 4, 2013, pp. 68-79.
Aizawa, "Bacterial flagella and type III secretion systems," FEMS Microbiology Letters, vol. 202, 2001 (published online Jul. 6, 2001), pp. 157-164.
Ashkenazy et al., "ConSurf 2010: calculating evolutionary conservation in sequence and structure of proteins and nucleic acids," Nucleic Acids Research, vol. 38, 2010 (published online May 16, 2010), pp. W529-W533.
Blocker et al., "Type III Secretion Systems and Bacterial Flagella: Insights into Their Function from Structural Similarities," Proceedings of the National Academy of Sciences of the United States of America, vol. 100, No. 6, Mar. 18, 2003, pp. 3027-3030 (5 pages provided).
Deane et al., "Crystal structure of Spa40, the specificity switch for the Shigella flexneri type III secretion system," Molecular Microbiology, vol. 69, No. 1, 2008 (published online May 29, 2008), pp. 267-276.
Ferris et al., "FlhB Regulates Ordered Export of Flagellar Components via Autocleavage Mechanism," The Journal of Biological Chemistry, vol. 280, No. 50, Dec. 16, 2005 (published, JBC Papers in Press, Oct. 24, 2005), pp. 41236-41242.
Ferris et al., "Flipping the switch: bringing order to flagellar assembly," Trends in Microbiology, vol. 14, No. 12, available online Oct. 25, 2006, pp. 519-526.
Fraser et al., "Substrate specificity of type III flagellar protein export in Salmonella is controlled by subdomain interactions in FlhB," Molecular Microbiology, vol. 48, No. 4, 2003, pp. 1043-1057.
Hirano et al., "Roles of FliK and FlhB in Determination of Flagellar Hook Length in Salmonella typhimurium," Journal of Bacteriology, vol. 176, No. 17, Sep. 1994, pp. 5439-5449.
Hirano et al., "Substrate Specificity Classes and the Recognition Signal for Salmonella Type III Flagellar Export," Journal of Bacteriology, vol. 185, No. 8, Apr. 2003, pp. 2485-2492.

(Continued)

*Primary Examiner* — Oluwatosin Ogunbiyi
(74) *Attorney, Agent, or Firm* — Birch, Stewart, Kolasch & Birch, LLP

(57) ABSTRACT

The present invention relates to a method for screening a compound that inhibits secretion of toxins into host-cell cytoplasm by virulent bacteria using a needle type III secretion system. The compound of the invention is selected by screening for a compound which interacts with a loop region of the cytoplasmic domain of the membrane protein FlhB from *Salmonella typhimurium* or a paralog thereof. Compositions including the compound of the invention, use of the compound, and methods of treating disorders caused by virulent bacteria are also provided.

4 Claims, 17 Drawing Sheets

(56) References Cited

OTHER PUBLICATIONS

Kutsukake et al., "Isolation and Characterization of FliK-Independent Flagellation Mutants from Salmonella typhimurium," Journal of Bacteriology, vol. 176, No. 24, Dec. 1994, pp. 7625-7629.

Lountos et al., "Atomic resolution structure of the cytoplasmic domain of Yersinia pestis YscU, a regulatory switch involved in type III secretion," Protein Science, vol. 18, 2009 (published online Jan. 6, 2009), pp. 467-474.

Minamino et al., "Components of the Salmonella Flagellar Export Apparatus and Classification of Export Substrates," Journal of Bacteriology, vol. 181, No. 5, Mar. 1999, pp. 1388-1394.

Minamino et al., "Domain Organization and Function of Salmonella FliK, a Flagellar Hook-length Control Protein," Journal of Molecular Biology, vol. 341, 2004, pp. 491-502.

Minamino et al., "Domain Structure of Salmonella FlhB, a Flagellar Export Component Responsible for Substrate Specificity Switching," Journal of Bacteriology, vol. 182, No. 17, Sep. 2000, pp. 4906-4914.

Minamino et al., "Interactions among components of the Salmonella flagellar export apparatus and its substrates," Molecular Microbiology, vol. 35, No. 5, 2000, pp. 1052-1064.

Minamino et al., "Molecular Characterization of the Salmonella typhimurium flhB Operon and Its Protein Products," Journal of Bacteriology, vol. 176, No. 24, Dec. 1994, pp. 7630-7637.

Mizuno et al., "The NMR Structure of FliK, the Trigger for the Switch of Substrate Specificity in the Flagellar Type III Secretion Apparatus," Journal of Molecular Biology, vol. 409, 2011 (available online Apr. 12, 2011), pp. 558-573.

Morris et al., "Kinetic Characterization of Salmonella FliK-FlhB Interactions Demonstrates Complexity of the Type III Secretion Substrate-Specificity Switch," Biochemistry, vol. 49, No. 30, 2010 (published online Jun. 29, 2010), pp. 6386-6393.

Veenendaal et al., "Small-Molecule Type III Secretion System Inhibitors Block Assembly of the Shigella Type III Secretion," Journal of Bacteriology, vol. 191, No. 2, Jan. 2009 (published ahead of print Nov. 7, 2008), pp. 563-570.

Wiesand et al.,"Structure of the Type III Secretion Recognition Protein YscU from Yersinia enterocolitica," Journal of Molecular Biology, vol. 385, 2009 (available online Oct. 19, 2008), pp. 854-866.

Williams et al., "Mutations in flik and flhB Affecting Flagellar Hook and Filament Assembly in Salmonella typhimurium," Journal of Bacteriology, vol. 178, No. 10, May 1996, pp. 2960-2970.

Zarivach et al., "Structural analysis of the essential self-cleaving type III secretion proteins EscU and SpaS," Nature, vol. 453, May 1, 2008, pp. 124-128.

Zhu et al., "Interactions among Membrane and Soluble Components of the Flagellar Export Apparatus of Salmonella," Biochemistry, vol. 41, No. 30, 2002 (published online Jul. 4, 2002), pp. 9516-9524.

Fig. 3a

```
              220        230        240        250        260        270
SalFlhB    KLRMSRQDIRDEFKESEGDPHVKGKIRQMQRAAAQRRMMEDVPKADVIVTNPTHYSVALQ
AquFlhB    KIMMSRRELKEDYKQLEGHPEVKSRIKARMRELAKSRMMAEVPKATVVITNPTHIAIALK
EscU       KMKMSKDEVKREAKDTDGNPEIKGERRRLHSEIQSGSLANNIKKSTVIVKNPTHIAICLY
YscU       ELKMSKDEIKREYKEMEGSPEIKSKRRQFHQEIQSGNMRENVKRSSVVVANPTHIAIGIL
SpaS       DMKMDKEEVKREMKEQEGNPEVKSKRREVHMEILSEQVKSDIENSRLIVANPTHITIGIY
Spa40      DMMMDKQEIKREYIEQEGHFETKSRRRELHIEILSEQTKSDIRNSKLVVMNPTHIAIGIY 280        290        300        310        320        330
SalFlhB    YDENKMSAPKVVAKGAGLIALRIREIGAEHRVPTLEAPPLARALYRHAEIGQQIPGQLYA
AquFlhB    YNPEKDKAPVVVAKGKGTIAQKIVEIAENYSIPVVRKPELARALYPAVEVGKEISPKFYK
EscU       YKLGETPLPLVIETGKDAKALQIIKLAELYDIPVIEDIPLARSLYKNIHKGQYITEDFFE
YscU       YKRGETPLPLVTFKYTDAQVQTVRKIAEEEGVPILQRIPLARALYWDALVDHYIPAEQIE
SpaS       FKPELMPIPMISVYETNQRALAVRAYAEKVGVPVIVDIKLARSLFKTHRRYDLVSLEEID
Spa40      FNPEIAPAPFISLIETNQCALAVRKYANEVGIPTVRDVKLARKLYKTHTKYSFVDFEHLD 340        350        360        370        380
SalFlhB    AVAEVLAWVWQLKRWRLAGGQRPPQPENLPVPEALDFMNEKNTDG
AquFlhB    AVAEIIAYVMFKKKKVYA---------------------------
EscU       PVAQLIRIA----IDLDY---------------------------
YscU       ATAEVLRWLERQNIEKQHSEML-----------------------
SpaS       EVLRLLVWLEEVENAGKDVIQPQENEVRH----------------
Spa40      EVLRLIVWLEQVENT-------------H----------------
```

SalFlhB$_C$ wt

Fig. 5c

SalFlhB$_C$ Δ(281-285)

N-terminus

FLAGELLAR AND NEEDLE COMPLEX (INJECTOSOME) LOOP AS ANTI BACTERIAL DRUG TARGET

CROSS REFERENCE TO RELATED APPLICATIONS

This application is the National Phase of PCT International Application No. PCT/JP2014/056082, filed on Feb. 27, 2014, which claims priority under 35 U.S.C. 119(e) to U.S. Provisional Application No. 61/770,046, filed on Feb. 27, 2013, all of which are hereby expressly incorporated by reference into the present application.

REFERENCE TO SEQUENCE LISTING SUBMITTED VIA EFS-WEB

This application includes an electronically submitted sequence listing in .txt format. The .txt file contains a sequence listing entitled "2017-07-27 0283-0389PUS1_ST25.txt" created on Jul. 27, 2017 and is 19,686 bytes in size. The sequence listing contained in this .txt file is part of the specification and is hereby incorporated by reference herein in its entirety.

FIELD OF THE INVENTION

The present invention relates to the type III secretion system of virulent bacteria, and more specifically, a method for screening a compound that inhibits secretion of toxins into host-cell cytoplasm by virulent bacteria using a needle type III secretion system.

BACKGROUND OF THE INVENTION

The bacterial flagellum is a large, complex structure that is used by many bacteria as a motility organelle. It consists of three main substructures: the basal body, the hook and the filament. Most of the flagellar proteins are initially localized inside of the cell and translocated across the cell membrane by the flagellum-specific secretion apparatus that is evolutionarily and structurally related to the virulence type III secretion system (Non-Patent Literature 1 and 2). Protein export by the flagellar type III secretion system is highly regulated. The secretion system first exports rod/hook type proteins until the hook reaches an appropriate length. After that the secretion system switches substrate specificity from hook-type export to filament-type export (Non-Patent Literature 3 and 4). In *Salmonella*, the substrate-specificity switch is controlled by two proteins: FliK and FlhB (Non-Patent Literature 5-7).

FlhB is an essential membrane protein of the flagellar type III secretion system. It consists of two domains: a hydrophobic N-terminal part (FlhB™) that is predicted to have four transmembrane helices, and a C-terminal cytoplasmic domain (FlhBc) (Non-Patent Literature 8). The two domains are connected by a flexible linker. This linker is a highly conserved part of the FlhB protein and is essential for the type III secretion system (TTSS). Deletions or point mutations in the linker region completely abort or significantly reduce secretion (Non-Patent Literature 9 and 10). The wild-type cytoplasmic domain of *Salmonella* FlhB undergoes autocatalytic cleavage between amino-acid residues Asn269 and Pro270 within a highly conserved NPTH sequence (Non-Patent Literature 11). This auto-cleavage is essential for the switching process (Non-Patent Literature 9 and 12). Mutation of Asn269 to Ala prevents cleavage and locks the export apparatus in the hook-type specificity state.

FlhB$_C$ has been shown to interact with several soluble components of the TTSS: FliH, FliI, FliJ (Non-Patent Literature 13), the cytoplasmic part of membrane protein FlhA (Non-Patent Literature 14) and the hook-length control protein FliK (Non-Patent Literature 15 and 16). Interaction of FlhB with FliK is suggested to be important for the substrate-specificity switching process (Non-Patent Literature 17). Cells with a deleted fliK gene produce an abnormally long hook, termed a "polyhook", without any filament attached (Non-Patent Literature 6).

PRIOR ART LITERATURES

Non-Patent Documents

[Non-Patent Literature 1] Aizawa, S.-I. (2001). FEMS Microbiol. Lett. 202, 157-164. Ashkenazy, H., Erez, E., Martz, E., Pupko, T., Ben-Tal, N. (2010). Nucleic Acids Res. 38, W529-W533.

[Non-Patent Literature 2] Blocker, A., Komoriya, K., Aizawa, S.-I. (2003). Proc. Natl. Acad. Sci. USA 100, 3027-3030.

[Non-Patent Literature 3] Minamino, T. and Macnab, R. M. (1999). J. Bacteriol. 181, 1388-1394.

[Non-Patent Literature 4] Hirano, T., Minamino, T., Namba, K., Macnab, R. M. (2003). J. Bacteriol. 185, 2485-2492.

[Non-Patent Literature 5] Kutsukake, K., Minamino, T., Yokoseki, T. (1994). J. Bacteriol. 176, 7625-7629.

[Non-Patent Literature 6] Hirano, T., Yamaguchi, S., Oosawa, K., Aizawa, S.-I. (1994). J. Bacteriol. 176, 5439-5449.

[Non-Patent Literature 7] Williams, A., Yamaguchi, S., Togashi, F., Aizawa, S.-I., Kawagishi, I., Macnab, R. M. (1996). J. Bacteriol. 178, 2960-2970.

[Non-Patent Literature 8] Minamino, T., Iino, T., Kutsukake, K. (1994). J. Bacteriol. 176, 7630-7637.

[Non-Patent Literature 9] Fraser, G. M., Hirano, T., Ferris, H. U., Devgan, L. L., Kihara, M., Macnab, R. M. (2003). Mol. Microbiol. 48, 1043-1057.

[Non-Patent Literature 10] Zarivach, R., Deng, W., Vuckovic, M., Felise, H. B., Nguyen, H. V., Miller, S. I., Finlay, B. B., Strynadka, N. C. J. (2008). Nature, 453, 124-127.

[Non-Patent Literature 11] Minamino, T., and Macnab, R. M. (2000a). J. Bacteriol. 182, 4906-4914.

[Non-Patent Literature 12] Ferris, H. U., Furukawa, Y., Minamino, T., Kroetz, M. B., Kihara, M., Namba, K., Macnab, R. M. (2005). J. Biol. Chem. 280, 41236-41242.

[Non-Patent Literature 13] Minamino, T., and Macnab, R. M. (2000b). Mol. Microbiol. 35, 1052-1064.

[Non-Patent Literature 14] Zhu, K., Gonzales-Pedrajo, B., Macnab, R. M. (2002). Biochemistry, 41, 9516-9524.

[Non-Patent Literature 15] Minamino, T., Saijo-Hamano, Y., Furukawa, Y., Gonzales-Pedrajo, B., Macnab, R. M., Namba, K. (2004). J. Mol. Biol. 341, 491-502.

[Non-Patent Literature 16] Morris, D. P., Roush, E. D., Thompson, J. W., Moseley, M. A., Murphy, J. W., McMurry, J. L. (2010). Biochemistry, 49, 6386-6393.

[Non-Patent Literature 17] Ferris, H. U., Minamino, T. (2006). Trends Microbiol. 14, 519-526.

[Non-Patent Literature 18] Deane, J. E., Graham, S. C., Mitchell, E. P., Flot, D., Johnson, S., Lea, S. M. (2008). Mol. Microbiol. 69, 267-276.

[Non-Patent Literature 19] Wiesand, U., Sorg, I., Amstutz, M., Wagner, S., van den Heuvel, J., Luhrs, T., Cornelis, G. R., Heinz, D. W. (2009). J. Mol. Biol. 385, 854-866.

[Non-Patent Literature 20] Lountos, G. T., Austin, B. P., Nallamsetty, S., Waugh, D. S. (2009). Protein Sci. 18, 467-474.

[Non-Patent Literature 21] Mizuno, S., Amida, H., Kobayashi, N., Aizawa, S.-I., Tate, S.-I. (2011). J. Mol. Biol. 409, 558-573.

[Non-Patent Literature 22] Veenendaal A. K. J, Sundin C., Blocker A. J. (2009). J. Bacteriol. 191(2) 563-570.

OBJECT OF THE INVENTION

Several structures of the cytoplasmic domain of FlhB paralogs from the needle TTSS have been published (Non-Patent Literature 10, and 18-20). However, no structural information about FlhB from the flagellar secretion system is available. Thus, it is an object of the present invention to clarify crystal structures of the cytoplasmic domain of flagellar FlhB from two organisms: *Salmonella typhimurium* and *Aquifex aeolicus*.

Based on the structural relationship between FlhB$_C$ of the flagellar secretion system and that of the needle type III secretion system utilized by a number of virulent bacteria for the secretion of toxins into the host-cell cytoplasm, it is also an object of the present invention to provide a method for identifying compounds that inhibits secretion of toxins into host-cell cytoplasm by virulent bacteria using the structural information of FlhBc.

SUMMARY OF THE INVENTION

The most important findings of the present invention is that flexibility of the large non-conserved loop in the globular domain of FlhB$_C$ is necessary for function of the whole secretion system. Deletion of the loop or its mutation to less flexible proline residues makes FlhB$_C$ more rigid and thus aborts or significantly reduces secretion. Taking into account similarity between the flagellar and needle proteins, this loop could be a promising target for creation of novel drugs against pathogenic bacteria, and the following inventions have been completed.

In one aspect of the present invention, there is provided a method for screening a compound that inhibits secretion of toxins into host-cell cytoplasm by virulent bacteria using a needle type III secretion system, the method comprising the steps of:

contacting a candidate compound with a C-terminal cytoplasmic domain of a membrane protein FlhB (FlhB$_C$) from *Salmonella typhimurium* or a paralog thereof, analyzing interaction of the candidate compound with or around a loop region of the cytoplasmic domain, and selecting a compound that reduces flexibility of the loop region or a linker that connects the transmembrane and cytoplasmic domains of FlhB or the paralog thereof, wherein the selected compound is indicated to inhibit the secretion of toxins by virulent bacteria.

In preferred embodiments, the virulent bacteria in the method of the invention is selected from the group consisting of *Salmonella typhimurium, Aquifex aeolicus, Yersinia pestis, Shigella flexneri*, enterohemorrhagic *Escherichia coli, Pseudomonas aeruginosa*, and *Vibrio parahaemolyticus*.

In particular embodiments, the paralog of the membrane protein FlhB from *Salmonella typhimurium* is EscU from *Escherichia coli*, YscU from *Yersinia pestis*, SpaS from *Salmonella typhimurium*, and Spa40 from *Shigella flexneri*.

In other particular embodiments, the loop region of the cytoplasmic domain of FlhB or the paralog thereof in the method of the invention consists of the amino acid residues ENKMS$_{281-285}$ (SEQ ID NO: 7) in *Salmonella* numeration.

In other particular embodiments, the compound that inhibits the secretion of toxins by virulent bacteria in the method of the invention is capable of binding to the loop region of the cytoplasmic domain of FlhB or the paralog thereof, or a flanking region thereof, wherein the flanking region comprising a conserved amino acid residue Tyr279 and Pro287 in *Salmonella* numeration.

In other particular embodiments, the interaction of the compound with or around the loop region of the cytoplasmic domain of FlhB or the paralog thereof in the method of the invention is determined whether or not the compound differentially binds to the membrane protein FlhB from *Salmonella typhimurium* and its Δ(281-285) mutant protein.

In other particular embodiments, the compound that inhibits the secretion of toxins by virulent bacteria in the method of the invention is an antibody or a fragment thereof, an aptamer or a small molecular compound.

In another aspect of the present invention, there is provided a method for screening a compound that inhibits secretion of toxins into host-cell cytoplasm by virulent bacteria using a needle type III secretion system, the method comprising the steps of:

i) selecting a candidate compound capable of interacting with a membrane protein FlhB from *Salmonella typhimurium* or a paralog thereof, by hydrogen bond between a loop region of the cytoplasmic domain of the FlhB or the paralog thereof and the candidate compound, ii) contacting the candidate compound with bacteria that has flagellar and needle type III secretion system, and iii) selecting a compound that reduces secretion of proteins from the bacteria and/or motility of the bacteria using the flagellar, wherein the selected compound is indicated to inhibit the secretion of toxins by virulent bacteria.

In one embodiment, the hydrogen bond between a loop region of the cytoplasmic domain of the membrane protein of FlhB or the paralog thereof and the candidate compound in the method of the invention is formed via at least one side chain of the amino acid residues ENKMS$_{281-285}$ (SEQ ID NO: 7) in *Salmonella* numeration.

In another aspect of the present invention, there is provided a compound identified by the method of the invention.

In another aspect of the present invention, there is provided a pharmaceutical composition for inhibiting secretion of toxins into the host-cell cytoplasm, comprising the identified compound of the invention, or a pharmaceutically acceptable salt thereof.

In one embodiment, the compound of the pharmaceutical composition of the invention is selected from the group of:

7-(2,3-dihydroxypropyl)-1,3-dimethyl-3,7-dihydro-1H-purine-2,6-dione 5-(3,4,5-Trimethoxybenzyl)pyrimidine-2,4-diamine and pharmaceutically acceptable salt thereof.

In another aspect of the present invention, a method of treating disorders caused by virulent bacteria using a needle type III secretion system, the method comprising:

contacting the bacteria with the pharmaceutical composition of the invention, and inhibiting the secretion of toxins by the virulent bacteria.

In another aspect of the present invention, there is provided a method for inhibiting secretion of toxins into the host-cell cytoplasm by virulent bacteria using a needle type III secretion system, the method comprising:

contacting the bacteria with the pharmaceutical composition of the invention, and inhibiting the secretion of toxins by the virulent bacteria.

In another aspect of the present invention, there is provided use of the composition of the invention for inhibiting secretion of toxins into the host-cell cytoplasm.

DETAILED DESCRIPTION OF THE INVENTION

Figure 1A:
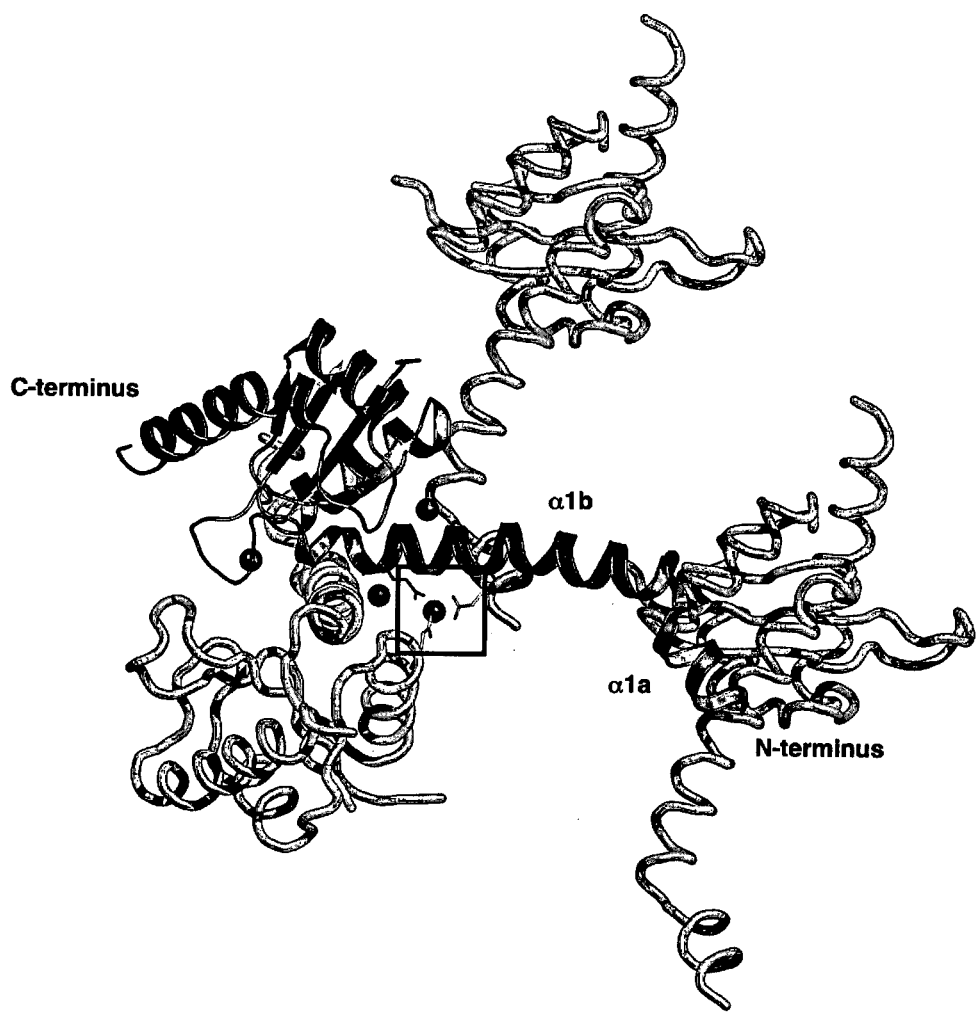
FIG. 1: Molecular packing in the crystal of *Salmonella* FlhB$_C$. (a) Asymmetric molecule and symmetry-related molecules are displayed in green and gray, respectively. Sodium ions are represented as magenta spheres, and zinc ions are shown as blue spheres. (b) Rotated enlarged view of the zinc-binding site (black box in FIG. 1a). The Fo-Fc electron density map is displayed in gray at a contour level of 5σ and was calculated without Zn atom.

Before the present invention is described in more detail below, it should be appreciated that the present invention is not limited to the particular methodology, protocols and reagents described herein as these may vary. It should be also appreciated that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art. For the purpose of the present invention, all references cited herein are incorporated by reference in their entireties.

The term "FlhB$_C$" used herein refers to a C-terminal cytoplasmic domain of FlhB, which is an essential membrane protein of the flagellar type III secretion system. In the context of present invention, the FlhB from *Salmonella typhimurium* is preferred. FlhB from *Salmonella typhimurium* and FlhB$_C$ thereof are described, e.g. in Non-Patent Literature 11. Typical example of an amino acid sequence of FlhB *Salmonella typhimurium* is provided in Swiss-Prot. Accession No. P40727 (SEQ ID NO: 1). For the purpose of present invention, the term "FlhB" also refers to a variant of FlhB from *Salmonella typhimurium* as long as the variant maintains its physiological activity and its crystalized property. The amino acid sequence of such variant may have an amino acid sequence at least 80%, 90% or 95% identical to SEQ ID NO: 1. The amino acid sequence of FlhB$_C$ is easily determined from the FlhB defined above. Preferably, the amino acid sequence of FlhB$_C$ is the amino acid position 219 to 383 of SEQ ID NO: 1 or variant thereof.

A paralog of FlhB from *Salmonella typhimurium* is also encompassed in the present invention. More specifically, the paralog include, but not limited to, FlhB from *Aquifex aeolicus* (a typical amino acid sequence is provided in Swiss-Prot. Accession No. 067813 (SEQ ID NO: 2)), EscU from *Escherichia coli* (a typical amino acid sequence is provided in (a typical amino acid sequence is provided in Swiss-Prot. Accession No. Q7DB59 (SEQ ID NO: 3)), YscU from *Yersinia pestis* (a typical amino acid sequence is provided in Swiss-Prot. Accession No. P69986 (SEQ ID NO: 4)), Spas from *Salmonella typhimurium* (a typical amino acid sequence is provided in Swiss-Prot. Accession No. P40702 (SEQ ID NO: 5)) and Spa40 from *Shigella flexneri* (a typical amino acid sequence is provided in Swiss-Prot. Accession No. Q6XVW1 (SEQ ID NO: 6)).

Cytoplasmic domain of the paralog is easily determined from full length amino acid sequence of such paralogs.

The term "virulent bacteria" used herein refers to any bacterium which bears needle type III secretion system. Such bacteria can secrete toxins including AB toxin. The Example of virulent bacteria includes, but not limited to, *Salmonella typhimurium, Aquifex aeolicus, Yersinia pestis, Shigella flexneri*, enterohemorrhagic *Escherichia coli, Pseudomonas aeruginosa*, and *Vibrio parahaemolyticus*.

A loop region of $FlhB_C$ or a paralog thereof of the present invention refers to the consecutive amino acid residues which constitute a long flexible loop connecting β2 and β3 strands in $FlhB_C$ or a paralog thereof. The length of the loop is longer than necessary just for connecting two β strands. This loop region may be determined using structural information obtained from crystals of $FlhB_C$ or a paralog thereof. In this context, exemplary crystals are those crystalized from $FlhB_C$ of *Salmonella typhimurium*, and from FlhBc *Aquifex aeolicus* which belongs $P4_22_12$ space group and C2 group, respectively. The crystal information of such crystals is shown in Table 1 and 2. Atomic coordinates and structure factors of structural information obtained from the above crystals are deposited in the PDB with accession codes 3B0Z and 3B1S for *Salmonella typhimurium*, and *Aquifex aeolicus*, respectively. The preferable loop region consists of the amino acid residues $ENKMS_{281-285}$ (SEQ ID NO: 7) in *Salmonella* numeration.

The loop region of FlhBc or a paralog thereof of the present invention can influences the flexibility of the N-terminal α-helix of $FlhB_C$ or a paralog thereof. "Flexibility" of $FlhB_C$ or a paralog thereof can be determined by any method known in the art. In one embodiment, flexibility of $FlhB_C$ or a paralog thereof can be determined by Molecular Dynamic Simulation (MDS) using structural information of $FlhB_C$ or a paralog, as disclosed in the Examples herein below. In another embodiment, the change of flexibility of $FlhB_C$ or a paralog thereof can be examined by the secretion assay or motility assay as disclosed in the Examples. In secretion assay, the reduction of the secretion activity of bacterium indicates the reduction of the flexibility of $FlhB_C$. Similarly in motility assay, the reduction of the motility activity of bacterium indicates the reduction of the flexibility of $FlhB_C$.

The term "flanking region" of the loop region used herein refers to the region comprises several amino acid sequence flanked to the N-terminal or C-terminal end of the loop region. The length of the flanking region may be 1 to 20, preferably 2 to 15, more preferably 5 to 10 amino acid length. Preferably, the flanking region comprises a conserved amino acid residue Tyr279 and Pro287 in *Salmonella* numeration.

As mentioned above, the present invention provides a method for screening a compound that inhibits secretion of toxins into host cell cytoplasm by virulent bacteria using a needle type III secretion system, the method comprising the step of:

contacting a candidate compound with a C-terminal cytoplasmic domain (FlhBc) of the membrane protein FlhB from *Salmonella typhimurium* or a paralog thereof, analyzing interaction of the candidate compound with or around a loop region of the cytoplasmic domain (FlhBc), and selecting a compound that reduces flexibility of the loop region, or a linker that connects the transmembrane and cytoplasmic domains of FlhB, wherein the selected compound is indicated to inhibit the secretion of toxins by virulent bacteria.

To contact a candidate compound with $FlhB_C$ or a paralog thereof, any technique known in the art can be used which enables the existence of the candidate compound and $FlhB_C$ or a paralog thereof at the same location. The candidate compound can be contacted with $FlhB_C$ in solid, in solution, or in atmosphere. The step of contacting can also be performed in silico, as described in detail herein below.

To analyze interaction of the candidate compound with or around a loop region of $FlhB_C$ or a paralog thereof. In accordance with the present invention, any technique known in the art can be used which enables the determination of the interaction manner between the candidate compound and $FlhB_C$ or a paralog thereof. Such technique includes, but not limited to, surface plasmon resonance such as Biacore, isothermal titration calorimetry (ITC), and fluorescence resonance energy transfer (FRET). The step of contacting can also be performed in silico, as described in detail herein below.

To select a compound that reduces flexibility of the loop region, or a linker that connects the transmembrane and cytoplasmic domains of FlhB, any technique known in the art can be used which enable the determination of the flexibility of $FlhB_C$. The MDS assay, secretion assay and motility assay disclosed in the Example can be used for this step.

For each step of the method of present invention, in silico technique known in the art can also be employed which uses the structural information of $FlhB_C$ disclosed herein. For example, computer modeling can be performed using a docking program such as GRAM, DOCK, HOOK or AUTODOCK (Dunbrack, et al. (1997) Folding & Design 2:27-42). Alternatively, GRID (Molecular Discovery Ltd., UK) software package can be used to perform a chemical-probe approach. These techniques enable the simulation of compounds which have strong affinity with or around a loop region of FlhBc or a paralog thereof.

Alternatively, Fragment Based Lead Discovery (FBLD) method (Rees D. C., Congreve M., Murray C. W., Can R. (2004). Nature Reviews Drug Discovery 3, 660-672) can be employed as in silico technique for the present invention. This method is the computational screening method using "fragment information" of commercially available compounds and structural information of interested protein. Primarily considered force in this method can be hydrogen bond. The detail of FBLD method will be explained in Examples herein below.

The candidate compound to be screened in the present invention can be any chemical entity. The candidate compound may include, but not limited to, an antibody, a fragment thereof, an aptamer and a small molecular compound.

A compound identified by the above screening method is also embraced in the present invention. The exemplary of selected compounds available commercially are listed in the following table:

| Compound | Structure | Chemical name |
|---|---|---|
| 47 | 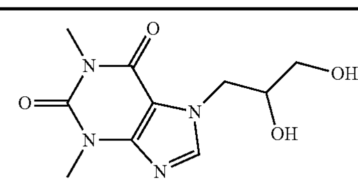 | 7-(2,3-dihydroxypropyl)-1,3-dimethyl-3,7-dihydro-1H-purine-2,6-dione |

| Compound | Structure | Chemical name |
|---|---|---|
| 48 | 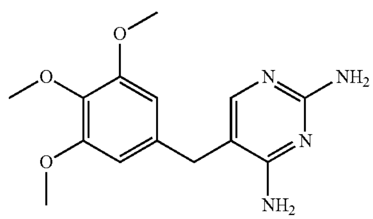 [SMILES: COc1cc(Cc2cnc(N)nc2N)cc(OC)c1OC] | 5-(3,4,5-Trimethoxybenzyl) pyrimidine-2,4-diamine |

The identified compound can be formulated to a pharmaceutical composition.

The production of the pharmaceutical compositions can be effected in a manner which will be familiar to any person skilled in the art by bringing the identified compound and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The dosage can be vary within wide limits and will, of course, be fitted to the individual requirements in each particular case. In general, in the case of oral administration a daily dosage of about 10 to 1000 mg per person of the identified compound should be appropriate, although the above upper limit can be exceeded when necessary.

The pharmaceutical composition comprising the identified compound or a pharmaceutically acceptable salt thereof can be used for treating or preventing disorders caused by virulent bacteria using a needle type III secretion system. The disorders may include, but not limited to, stomach ache, diarrhea, nausea, vomit and convulsion. The pharmaceutical composition can be also used for inhibiting secretion of toxins into the host-cell cytoplasm by the virulent bacteria.

Treatment or prevention typically involves administering to a subject in need of treatment a pharmaceutical composition containing an effective dose of a compound identified in the screening method of the invention. In most cases this will be a human being, but treatment of agricultural animals. e.g., livestock and poultry, and companion animals, e.g., dogs, cats and horses, is expressly covered herein. The selection of the dosage or effective amount of a compound is that which has the desired outcome of preventing, reducing or reversing at least one sign or symptom of the disorder being treated.

The invention is described in greater detail by the following non-limiting examples.

EXAMPLES

Example 1: Materials and Methods 1.1. Structure Determination

Details of purification of *Salmonella* and *Aquifex* $FlhB_C$, crystallization and data collection were described (Meshcheryakov, V. A. and Samatey, F. A. (2011). Acta Cryst. F67, 808-811; Meshcheryakov, V. A., Yoon, Y.-H. and Samatey, F. A. (2011). Acta Cryst. F67, 280-282). Both structures were solved by multiwavelength anomalous diffraction (MAD) using the program SHELXD (Sheldrick, G. M. (2008). Acta Cryst. A64, 112-122). Initial protein models were built automatically with Buccaneer (Cowtan, K. (2006). Acta Cryst. D62, 1002-1011) from the CCP4 package (Winn, M. D., Ballard, C. C., Cowtan, K. D., Dodson, E. J., Emsley, P., Evans, P. R., Keegan, R. M., Krissinel, E. B., Leslie, A. G. W., McCoy, A., McNicholas, S. J., Murshudov, G. N., Pannu, N. S., Potterton, E. A., Powell, H. R., Read, R. J., Vagin, A., Wilson, K. S. (2011) Acta Cryst. D67, 235-242). The models were refined through an iterative combination of refinement with Refmac5 (Murshudov, G. N., Skubak, P., Lebedev, A. A., Pannu, N. S., Steiner, R. A., Nicholls, R. A., Winn, M. D., Long, F., Vagin, A. A. (2011) Acta Cryst. D67, 355-367) and manual model building in COOT (Emsley, P., Lohkamp, B., Scott, W. G., Cowtan, K. (2010). Acta Cryst. D66, 486-501). In the case of *Salmonella* $FlhB_C$, TLS refinement was performed in the final stages with two TLS groups per $FlhB_C$ molecule (residues 229-269 and 270-353) (Painter, J. and Merritt, E. A. (2006) Acta Cryst. D62, 439-450). Structural figures were made in PyMOL (world wide web at pymol.org).

1.2. DNA Manipulation and Motility Assay

Mutations of *S. typhimurium* flhB carried by plasmid pMM26 (Non-Patent Literature 11) were done as previously described (Wang, W., Malcolm, B. A. (1999). BioTechniques, 26, 680-682). For the motility assay, freshly transformed *Salmonella* cells were inoculated as colonies directly into soft tryptone agar containing 0.35% (w/v) agar and incubated at 303 K.

1.3. Preparation of the Whole Cell and Culture Supernatant Fractions and Immunoblotting

*Salmonella* cells MKM50 (ΔflhB strain) (Non-Patent Literature 9) carrying an appropriate plasmid were incubated at 310 K in LB medium containing 100 µg $ml^{-1}$ of ampicillin until optical density OD600 reached 1.4-1.5. Aliquots of culture containing a constant amount of cells were centrifuged.

Cell pellets were suspended in an equal volume of SDS-loading buffer. Proteins in the culture supernatant were precipitated by 10% trichloroacetic acid and suspended in SDS-loading buffer. After SDS-PAGE, proteins were detected with anti-FlgE and anti-FliC antibodies using a WesternBreeze® chromogenic immunodetection kit (Invitrogen).

1.4. Molecular Dynamics Simulation

Molecular dynamics (MD) simulations were performed using the SCUBA (Simulation Codes for huge Biomolecular Assembly) program package (Ishida, H., Higuchi, M., Yonetani, Y., Kano, T., Joti, Y., Kitao, A., Go, N. (2006). Annual Report of the Earth Simulator Center, 237-239). The AMBER ff99SB force-field (Hornak, V., Abel, R., Okur, A., Strockbine, B., Roitberg, A., Simmerling, C. (2006) Proteins: Structure, Function and Bioinformatics, 65, 712-725) was used for the protein. The simulated systems were solvated with the SPC/E water molecules (Berendsen, H. J. C., Grigera, J. R., Straatsma, T. P. (1987). J. Phys. Chem. 91, 6269-6271) with 100 mM KCl in the periodic boundary separated by at least 12 Å from the $FlhB_C$ molecule in the initial stage. After energy minimization and 0.27 ns MD simulation to adjust the temperature and pressure of the system to 300 K and 1 atm with positional restraints, 40 ns MD simulation was performed without restraints in the canonical ensemble. The last 20 ns trajectory was used for the analysis. A shifted-force cutoff of real space non-bonded energy was made at 12 A and the particle-particle-particle-mesh (PPPM) method (Deserno, M., Holm, C. (1998). J. Chem. Phys. 109, 7678-7693) was employed for electrostatic energy calculation in Fourier space. Integration of the equation of motion was carried out using the multi-time step method XORESPA (Martyna, G. J., Tuckerman, M. E., Tobias, D. J., Klein, M. L. (1996). Mol. Phys. 87, 1117-1157) in the canonical ensemble. Integrations of fast (bond and angle), medium (torsion and real space non-bonded) and slow (Fourier space non-bonded) energy terms were performed every 0.5, 1.0 and 2.0 fs, respectively.

1.5. Accession Numbers

Atomic coordinates and structure factors are deposited in the PDB with accession codes 3B0Z and 3B1S for *Salmonella* and *Aquifex* $FlhB_C$, respectively. The structures reported here are explained in interactive 3D at http://Proteopedia.Org/w/Samatey.

Results

Example 2: Flagellar $FlhB_C$ Structure Description

*Salmonella* (Sal $FlhB_C$) and *Aquifex* (Aqu $FlhB_C$) $FlhB_C$ structures were solved by multiwavelength anomalous diffraction (MAD) using selenomethionine derivatives (Meshcheryakov et al., 2011; Meshcheryakov and Samatey, 2011) (Table 1).

TABLE 1

X-ray data collection and refinement statistics. Values in parentheses indicate statistics for the highest resolution shell. MAD data collection statistics for *Salmonella* $FlhB_C$ was published in Meshcheryakov and Samatey, 2011.

|  | *Salmonella* $FlhB_C$ Native | Native | Aquifex $FlhB_C$ | | SeMet derivative | |
| --- | --- | --- | --- | --- | --- | --- |
| Data collection | | | | | | |
| Space group | $P4_22_12$ | C2 | | | C2 | |
| Cell dimensions | | | | | | |
| a, b, c (Å) | 49.1, 49.1, 143.1 | 114.6, 33.8, 122.4 | | | 113.4, 33.6, 122.2 | |
| α, β, γ (°) | 90, 90, 90 | 90, 107.8, 90 | | | 90, 107.9, 90 | |
| Molecules/A.U.$^a$ | 1 | 3 | Peak | Inflection | | Remote |
| Wavelength (Å) | 0.9 | 0.9 | 0.9791 | 0.97936 | | 0.99508 |
| Resolution (Å) | 40.45-2.45 (2.58-2.45) | 47.76-2.55 (2.69-2.55) | 50-3.0 (3.16-3.0) | 50-3.0 (3.16-3.0) | | 50-3.0 (3.16-3.0) |
| $R_{merge}^b$ | 0.075 (0.380) | 0.056 (0.386) | 0.094 (0.452) | 0.069 (0.407) | | 0.064 (0.368) |
| I/σI | 16.2 (5.7) | 12.5 (3.4) | 7.6 (2.4) | 9.9 (3.0) | | 10.5 (3.2) |
| Completeness (%) | 98.8 (100) | 99.3 (100) | 100 (100) | 100 (100) | | 100 (100) |
| Redundancy | 7.7 (7.9) | 3.7 (3.8) | 3.6 (3.7) | 3.7 (3.7) | | 3.7 (3.7) |
| Refinement | | | | | | |
| Resolution (Å) | 28.07-2.45 | 29.75-2.55 | | | | |
| $R_{work}/R_{free}$ | 23.1/24.7 | 24.1/26.2 | | | | |
| No. atoms | | | | | | |
| Protein | 992 | 2707 | | | | |
| Ligand/ion | 4 | 0 | | | | |
| Water | 20 | 48 | | | | |
| Wilson plot B-factor | 79.3 | 83.7 | | | | |
| Average B-factor | | | | | | |
| Protein | 78.8 | 73.6 | | | | |
| Ligand/ion | 77.2 | N/A | | | | |
| Water | 39.3 | 61.2 | | | | |
| R.m.s deviations | | | | | | |
| Bond lengths (Å) | 0.021 | 0.019 | | | | |
| Bond angles (°) | 2.090 | 1.844 | | | | |

TABLE 1-continued

X-ray data collection and refinement statistics. Values in parentheses
indicate statistics for the highest resolution shell. MAD data collection
statistics for *Salmonella* FlhB$_C$ was published in Meshcheryakov
and Samatey, 2011.

| | *Salmonella* FlhB$_C$ Native | Native | Aquifex FlhB$_C$ | SeMet derivative |
|---|---|---|---|---|
| Ramachandran plot (%) | | | | |
| Most favoured | 97.5 | 99.7 | | |
| Additionally allowed | 2.5 | 0.3 | | |
| Disallowed | 0 | 0 | | |

[a] A.U. (asymmetric unit).
[b] R$_{merge}$ = $\Sigma_{hkl}\Sigma_i|I_i(hkl) - \langle I(hkl)\rangle| / \Sigma_{hkl}\Sigma_i I_i(hkl)$, where I$_i$(hkl) is the intensity of the i-th measurement of reflection hkl and <I(hkl)> is the mean value of I$_i$(hkl) for all i measurements.

Sal FlhB$_C$ and Aqu FlhB$_C$ crystals belonged to different space groups, P42212 and C2, respectively. In the case of the Aqu FlhB$_C$ crystal there were three protein molecules in the asymmetric unit. Three molecules in the asymmetric unit are very similar, with RMSD for pairwise superposition ranging 0.40-0.76 Å. Each molecule consisted of two polypeptide chains resulting from proteolytic cleavage after Asn263. For all molecules no electron density was seen for the residues 213-231 on N-terminus; depending on the molecule, from 2 to 6 residues on C-terminus was disordered.

Figure 1B:
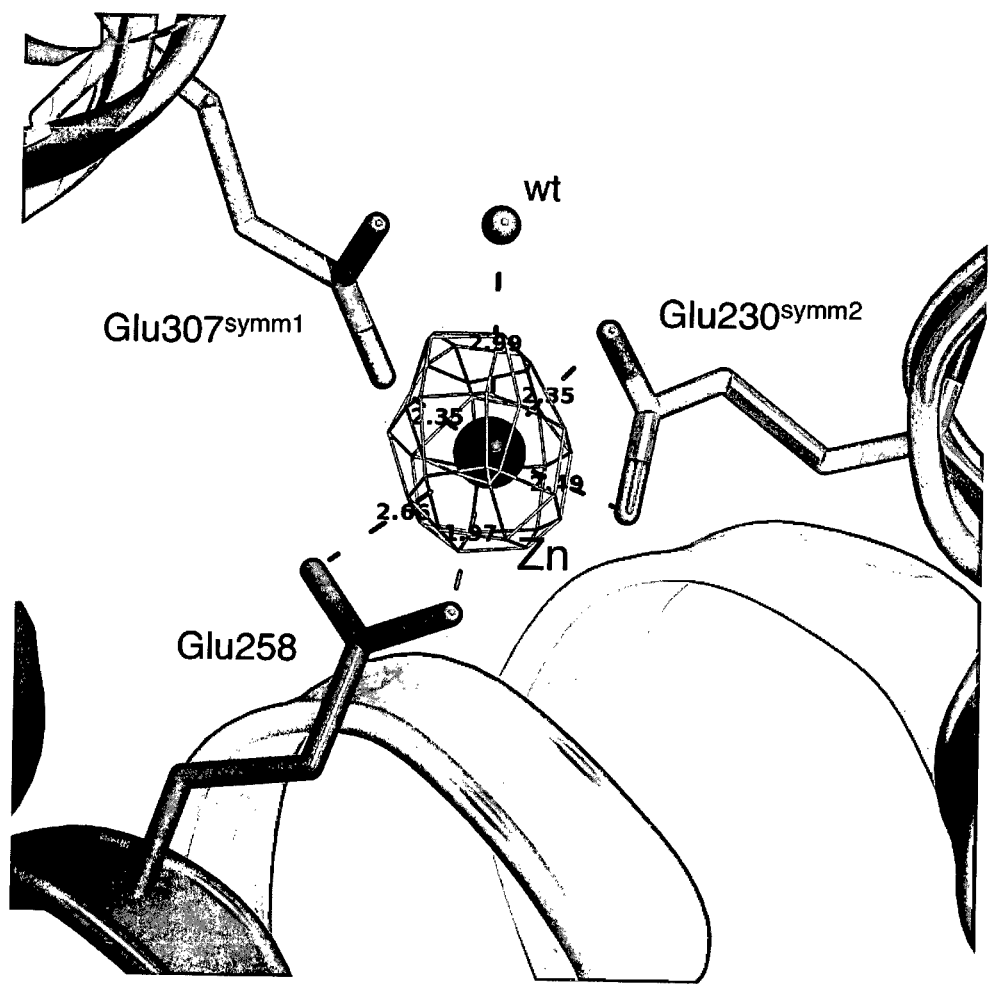

In the case of Sal FlhB$_C$, the final model comprised residues 229-353 out of 219-383 in the crystallized protein, with a cleavage after Asn269. No electron density was seen for the residues 219-228 and 354-383. The model of *Salmonella* FlhB$_C$ included two Zn and two Na ions (FIG. 1a). All these atoms mediated intermolecular interactions in the crystal lattice. Zn$^{2+}$ was added to crystallization solution, and it was necessary to obtain well diffracting crystals. Analysis of the crystallographic packing showed that one of the zinc ions coordinated three glutamate residues from three symmetry-related SalFhB$_C$ molecules: Glu230, Glu258, and Glu307 (FIG. 1b). This interaction makes N-terminal helix α1, one of the most flexible parts of *Salmonella* FlhB$_C$ (see below), to be fixed between two symmetrical molecules.

Figure 2A:
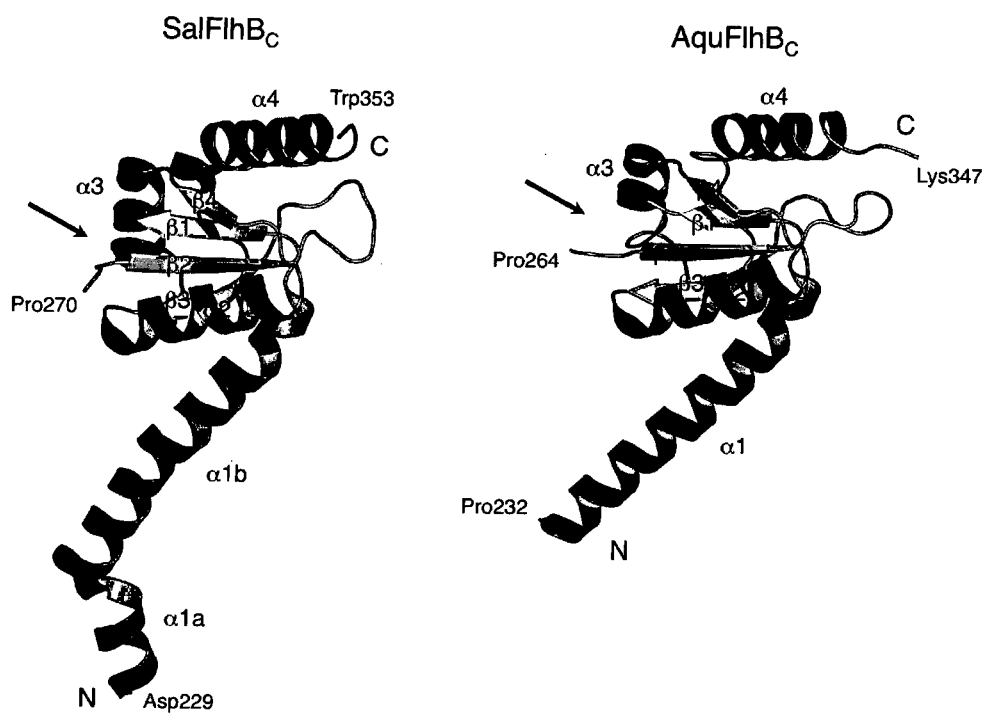
FIG. 2: Structure of flagellar FlhB$_C$. (a) Ribbon representation of the crystal structure of *Salmonella* and *Aquifex* FlhB$_C$. (b) Electrostatic potential mapped on the surface of *Salmonella* FlhB$_C$. Electrostatics was calculated using APBS software (Baker, N. A., Sept, D., Joseph, S., Holst, M. J., McCammon, J. A. (2001). Proc. Natl. Acad. Sci. USA 98, 10037-10041) and plotted at ±5 kT e-1. (c) Evolutionarily conserved residues of FlhB$_C$. The figure was prepared with ConSurf (http://consurf.tau.ac.il/) (Ashkenazy et al., 2010). Residues are colored accordingly to the conservation in amino acid sequences of 200 different FlhB proteins. Arrows mark position of the autocleavage site between β1 and β2.

Both the *Salmonella* and *Aquifex* FlhB$_C$ structures showed very similar folds with an RMSD of 1.03 A for 102 Cα atoms (FIG. 2a). Flagellar FlhB$_C$ consisted of a globular domain composed of a four-stranded β-sheet, surrounded by four α-helices. The globular domain was preceded by a long Nterminal α-helix (α1) that connects the cytoplasmic globular part of FlhB to transmembrane domain. The α1 helix engaged in a crystal contact in both the *Salmonella* and *Aquifex* FlhB$_C$ crystals, which may affect its orientation relative to the globular domain. However, these crystal contacts differed. In Sal FlhB$_C$ crystal, al contacted primarily α1 and α2 of adjacent molecules, while in Aqu FlhB$_C$ crystal, α1 contacted primarily α4 and the cleavage site between β1 and β2.

The major difference between Sal FlhB$_C$ and Aqu FlhB$_C$ is the N-terminal region. In the model of Sal FlhB$_C$, helix α1 was longer and had a kink at a very conserved residue Gly236. However, a longer helix with a kink was not excluded in Aqu FlhB$_C$, where highly conserved Gly230 occurred just 2 residues into the disordered segment 213-231 present in the crystallized protein but absent in the model. Although the kink may be due to the crystal packing, our data showed potential flexibility of the linker around this conserved glycine residue. The importance of such flexibility was previously shown for EscU, an FlhB paralog from the needle TTSS. Mutation of Gly229 (which corresponds to Gly236 of SalFlhB) to less flexible proline in EscU completely abolished secretion (Non-Patent Literature 10).

Figure 2B:
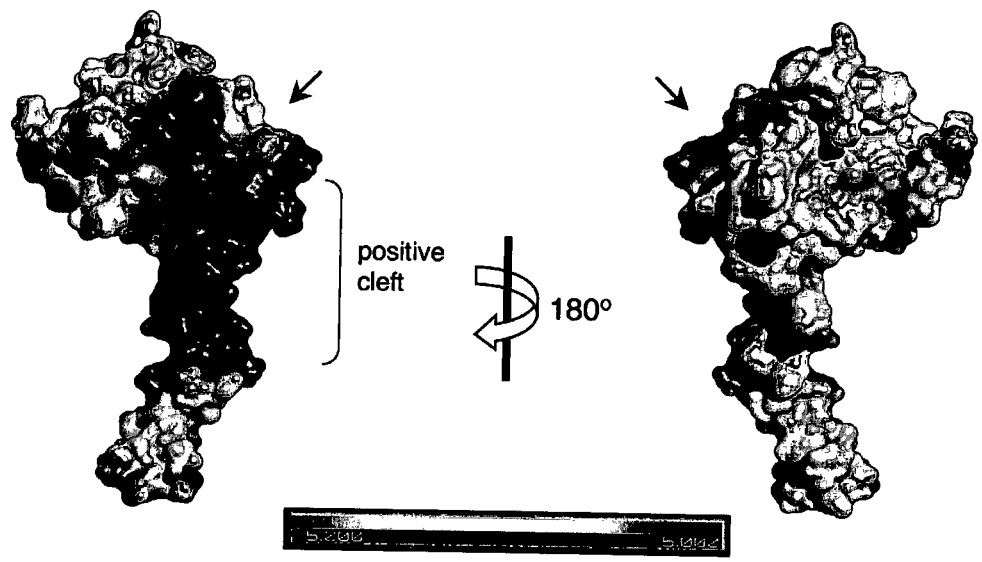
Figure 2C:
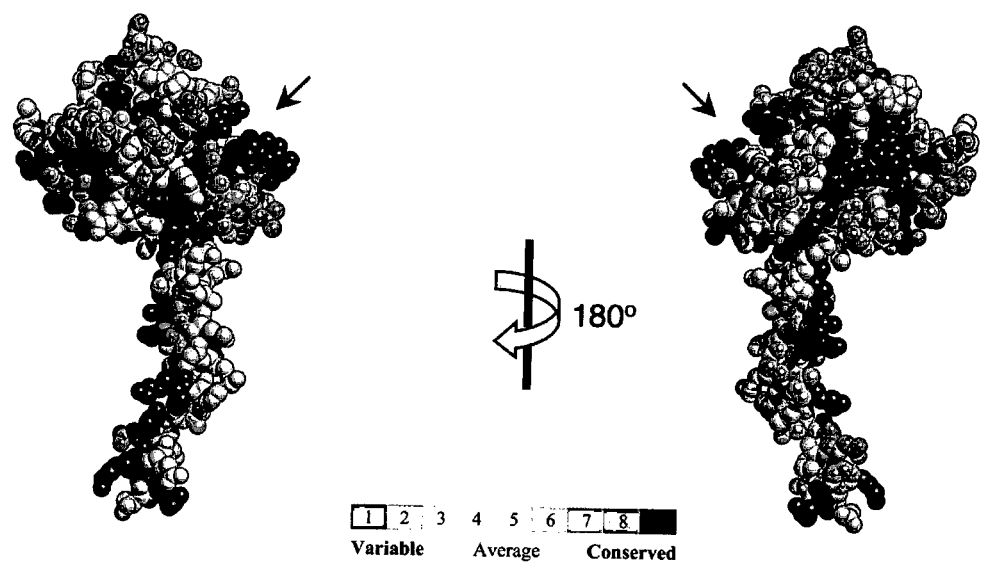

The conserved NPTH autocleavage site was exposed on a surface between strands β1 and β2. Both *Salmonella* and *Aquifex* FlhB$_C$ showed different conformations of PTH region that suggested its flexibility. This was very different from the needle paralogs. In all known paralog structures, the PTH region has the same orientation, which is stabilized by the contacts with surrounding residues (Non-Patent Literature 10; Non-Patent Literature 18; Non-Patent Literature 19; Non-Patent Literature 20). It was difficult to say for the moment whether the greater flexibility of the PTH site in flagellar FlhB$_C$ has any functional meaning. In Sal FlhB$_C$, the PTH region, together with adjacent residues in the globular domain and the C-terminal part of the linker α-helix, formed a positively charged cleft (FIG. 2b). A similar positive cleft was present also in Aqu FlhB$_C$. Such a cleft might be a potential recognition site for proteins secreted by the flagellar secretion system. The autocleavage of FlhB has been suggested to create an interaction site for other components of the type III secretion system (Non-Patent Literature 10; Non-Patent Literature 18). In particular, there is a model describing the binding of FliK to the cleaved NPTH loop of FlhB (Non-Patent Literature 21). However, the linker helix, which was one of the most conserved parts of FlhB protein (FIG. 2c), could also participate in the recognition of secreted proteins, since deletions or point mutations in this region of FlhB completely block secretion (Non-Patent Literature 9; Non-Patent Literature 10).

Example 3: Comparison with Needle Paralog Structures

Figure 3B:
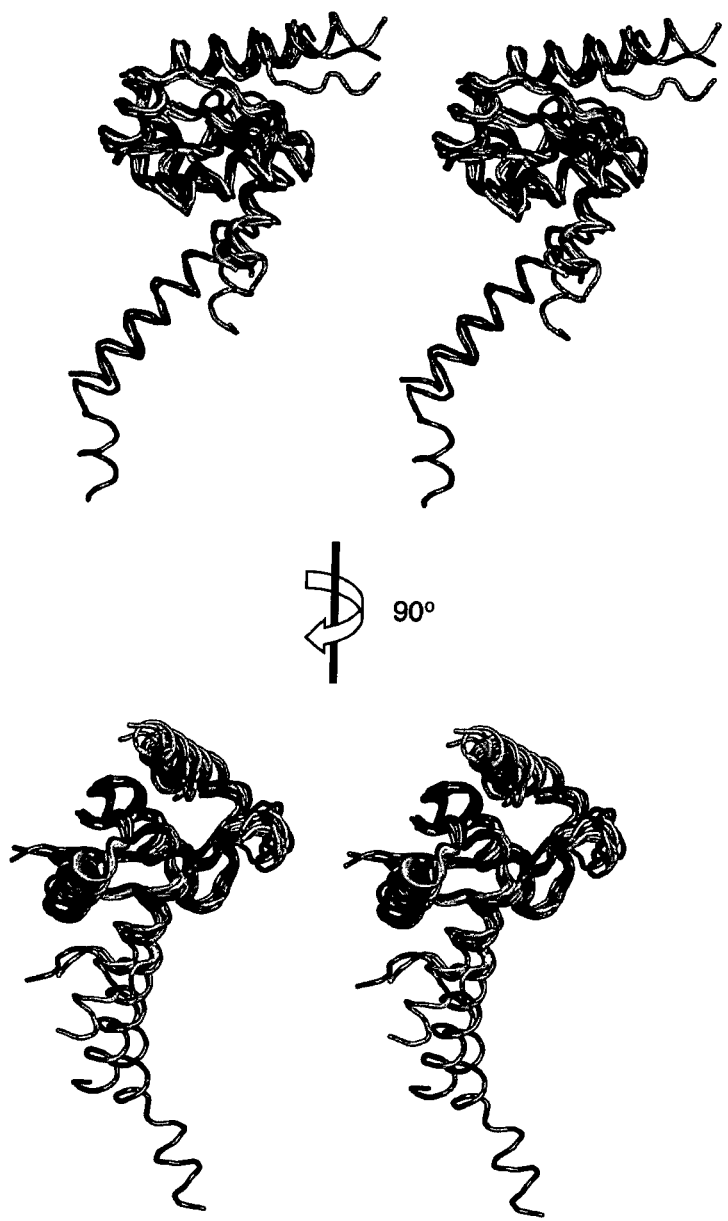
FIG. 3: Comparison of flagellar FlhB$_C$ and its paralogs from needle type III secretion system. (a) Multiple sequence alignment of FlhB$_C$ from *S. typhimurium* (Sal FlhB$_C$) (SEQ ID NO: 1) (Swiiss-Prot. Accession number P40727) with FlhB$_C$ from *A. aeolicus* (Aqu FlhB$_C$) (O67813) (SEQ ID NO: 2), EscUC from *E. coli* (Q7DB59) (SEQ ID NO:3), YscUC from *Yersinia pestis* (P69986) (SEQ ID NO: 4), SpaSC from *S. typhimurium* (P40702) (SEQ ID NO: 5) and Spa40C from *Shigella flexneri* (Q6XVW1) (SEQ ID NO: 6). Identical residues are boxed in red; similar residues are colored red. Alignment was done with Clustal W (Larkin, M. A., Blackshields, G., Brown, N. P., Chenna, R., McGettigan, P. A., McWilliam, H., Valentin, F., Wallace, I. M., Wilm, A., Lopez, R., Thompson, J. D., Gibson, T. J., Higgins, D. G. (2007). Bioinformatics, 23, 2947-2948; Goujon, M., McWilliam, H., Li, W., Valentin, F., Squizzato, S., Paern, J., Lopez, R. (2010). Nucleic Acids Res. 38, W695-699). (b) Stereo views of the superposition of *Salmonella* FlhB$_C$ (blue) (PDB ID: 3B0Z), *Aquifex* FlhB$_C$ (red) (PDB ID: 3B1S), EscUC (orange) (PDB ID: 3BZO), YscUC (gray) (PDB ID: 2JLI), SpaSC (green) (PDB ID: 3C01) and Spa40C (purple) (PDB ID: 2VT1).

Despite a low sequence identity (FIG. 3a), the overall structure of flagellar FlhBc was very similar to the structures of the paralogs from the needle secretion system: EscUC, SpaSC, YscUC, and Spa40C (FIG. 3b). The obvious difference between these proteins was the linker region between the N-terminal transmembrane domain and the globular cytoplasmic domain. All proteins showed a big difference in the conformation of their N-terminal parts, indicating flexibility of this region of the molecule. In our structures no electron density was observed for residues 219-228 of Sal FlhB$_C$ and residues 213-231 of Aqu FlhB$_C$, which was consistent with flexibility of this part of FlhB$_C$.

However, the remaining of the residues of the linker formed a well-defined α-helix, which, in the case of Sal FlhB$_C$, was kinked at position Gly236. In contrast to the needle paralogs, it might be a general property of flagellar FlhB to have a more stable linker helix.

Proteins of the FlhB family exhibit significant variation in length mainly because of differences at the C-terminus. For instance, *Salmonella* FlhB is longer than *Aquifex* protein by 33 amino acids. However, these additional residues (residues 354-383) were not visible in the electron density map suggesting that they are unfolded. This region in SalFlhB was rich with proline residues making it unlikely to form any stable structure. The function of the elongated C-terminal part of FlhB is not known, but it is dispensable for motility (Non-Patent Literature 5). It apparently participates in the regulation of secretion because C-terminal truncation of *Salmonella* FlhB can partially suppress the phenotype of ΔfliK (Non-Patent Literature 5 and 7). However, it is unlikely to directly interact with FliK since the truncation has almost no effect in a wild-type fliK background (Non-Patent Literature 7).

Figure 4A:
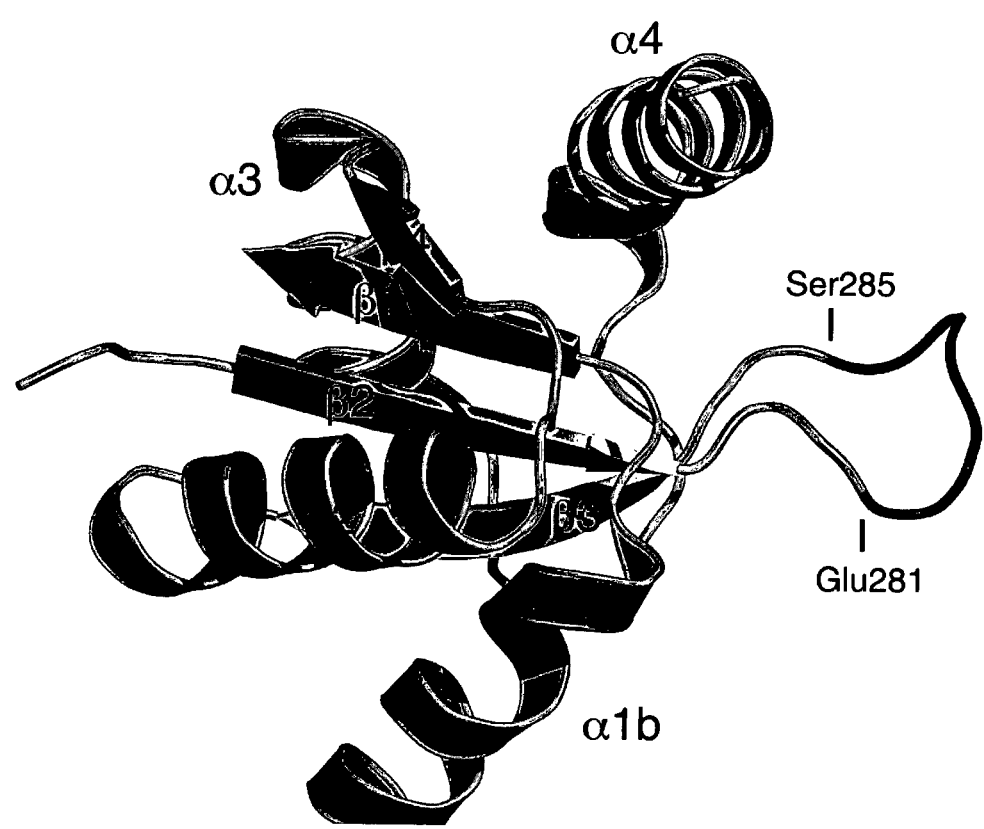
FIG. 4: Effect of mutations of the region ENKMS$_{281-285}$ (SEQ ID NO: 7) of *Salmonella* FlhB on the protein function. (a) Ribbon representation of *Salmonella* FlhB$_C$; the region is in black. (b) Ability of FlhB variants with modified ENKMS (SEQ ID NO: 7) region to complement a ΔflhB *Salmonella* strain MKM50. Motility was carried out on semi-solid agar plates at 303 K for 5 h. FlhB products were: 1) none, empty vector, 2) wild-type FlhB, 3) FlhB Δ(281-285), 4) FlhB AAAAA$_{281-285}$ (SEQ ID NO: 8), and 5) FlhB PPPPP$_{281-285}$. (SEQ ID NO: 9), (c) Immunoblotting using anti-FlgE and anti-FliC antibodies on the whole cell and culture supernatant fractions from MKM50 *Salmonella* strain producing different FlhB variants.
Figure 4B:
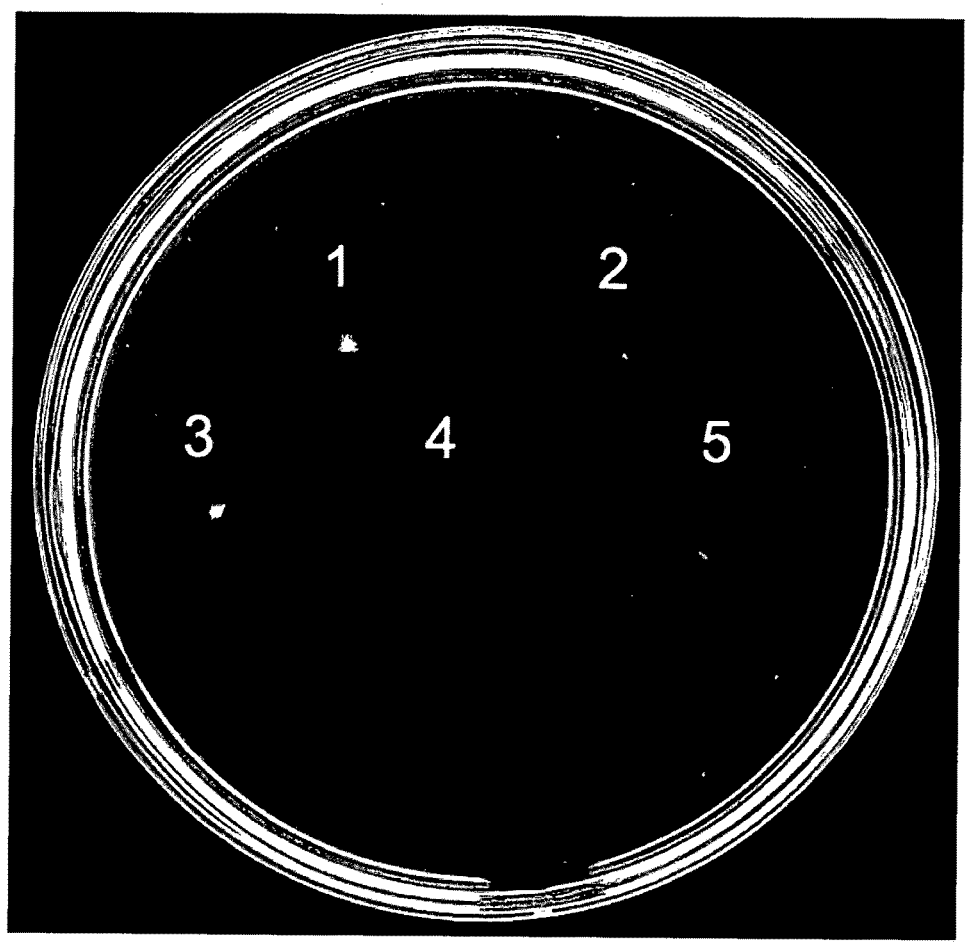
Figure 4C:
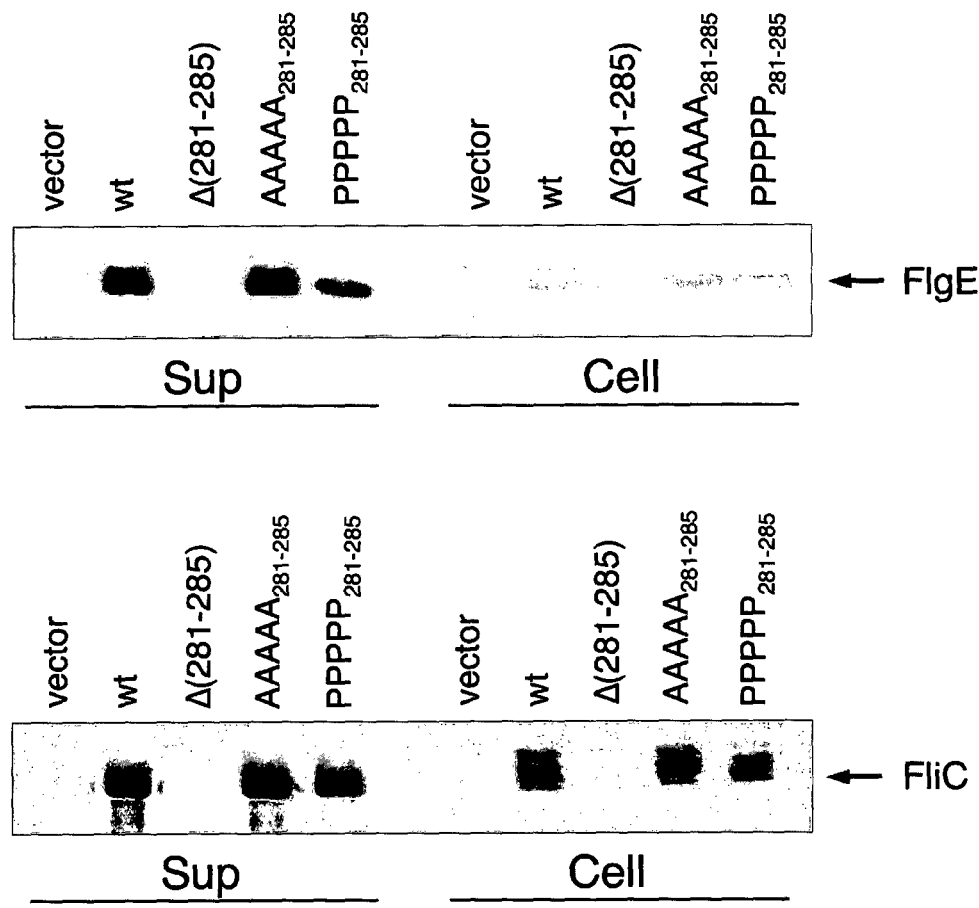
Figure 5A:
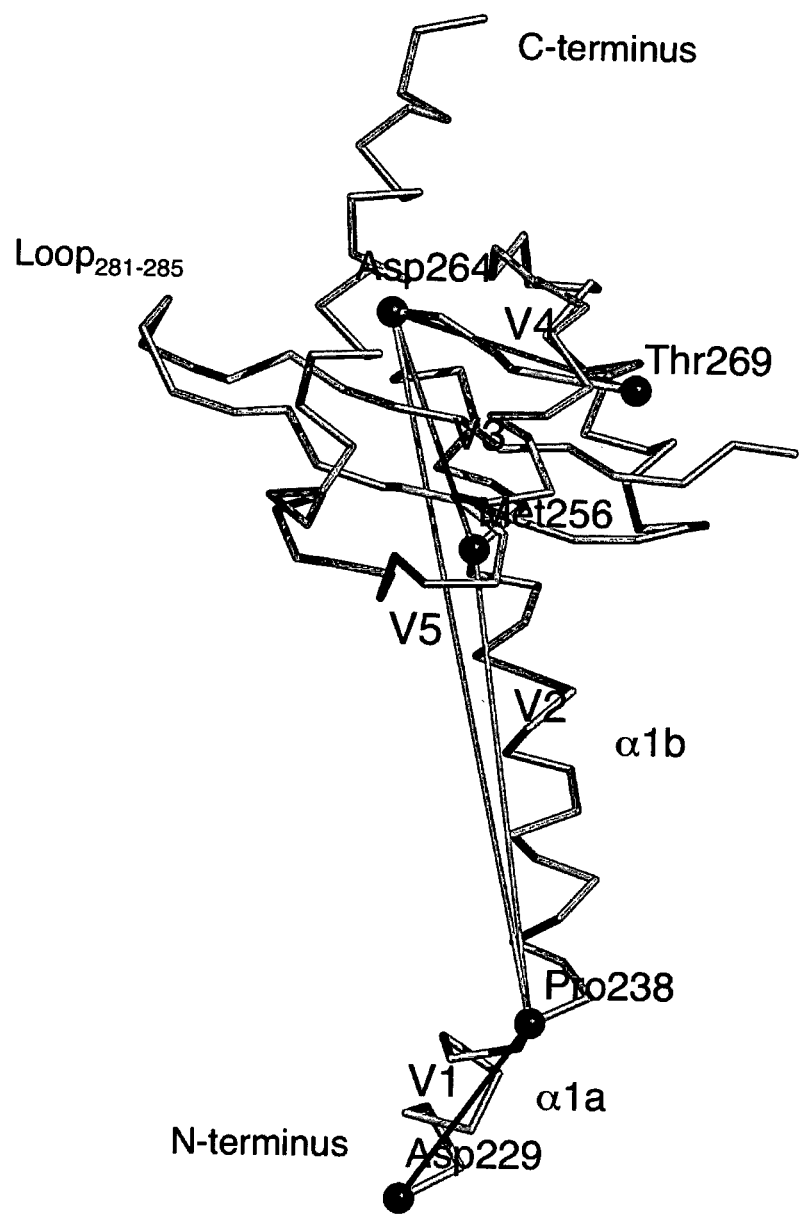
FIG. 5: Flexibility of the N-terminal α-helix of *Salmonella* FlhB$_C$ observed in MD simulation. (a) Key residues and vectors used for MD analysis in Table 2. The vectors connecting residues 229-238, 238-256, 256-264, 265-269 and 238-264 are defined as V1-V5, respectively. (b-e) Structure variations of the N-terminal α-helix during MD when the globular domain is superimposed for (b) the wild-type FlhB$_C$, (c) FlhB$_C$ Δ(281-285), (d) FlhB$_C$ AAAAA$_{281-285}$ (SEQ ID NO: 8) and (e) FlhB$_C$ PPPPP$_{281-285}$ (SEQ ID NO: 9). For each case, six snapshots were chosen based on the maximum and minimum values of D, θ14 and χ5 (see Table 2 for their definitions).
Figure 5B:
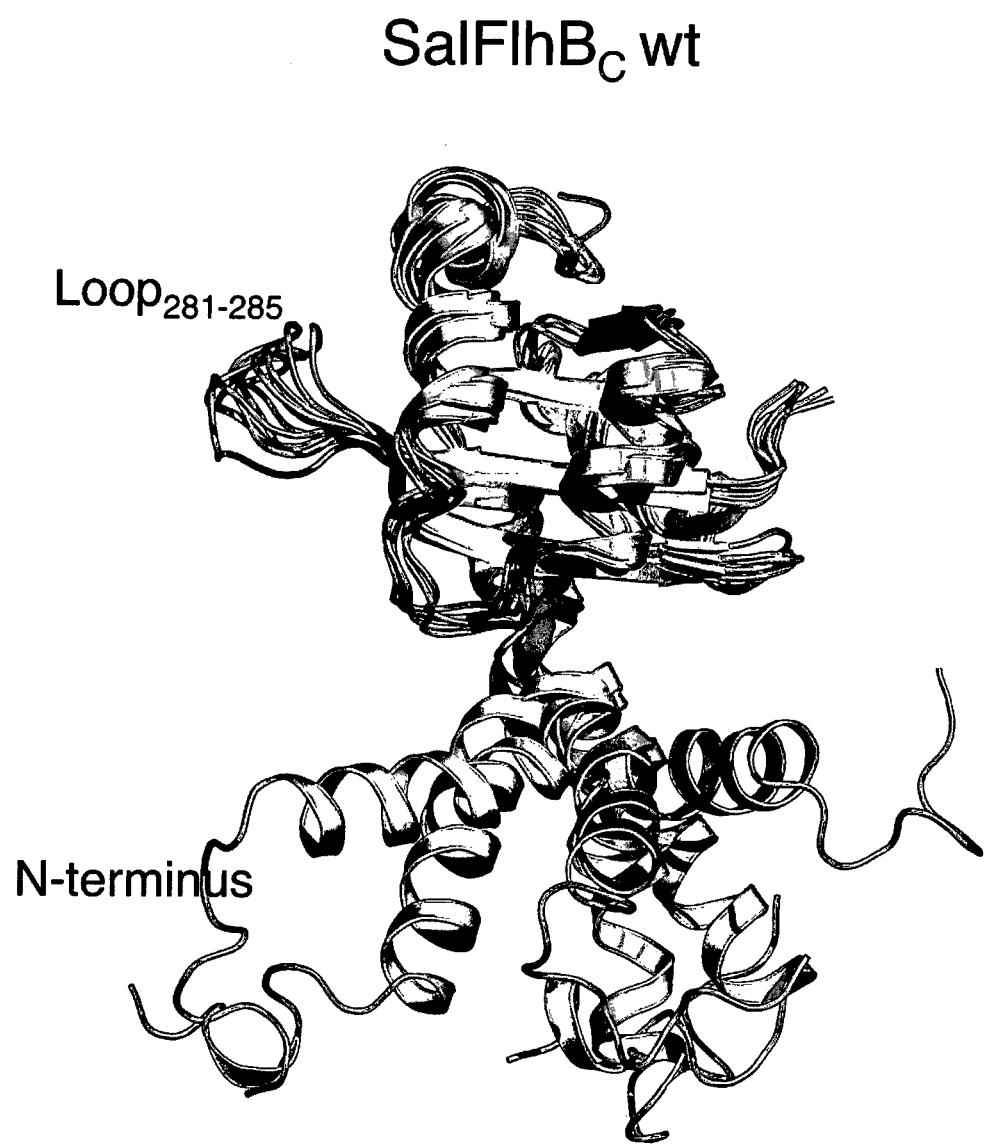
Figure 5D:
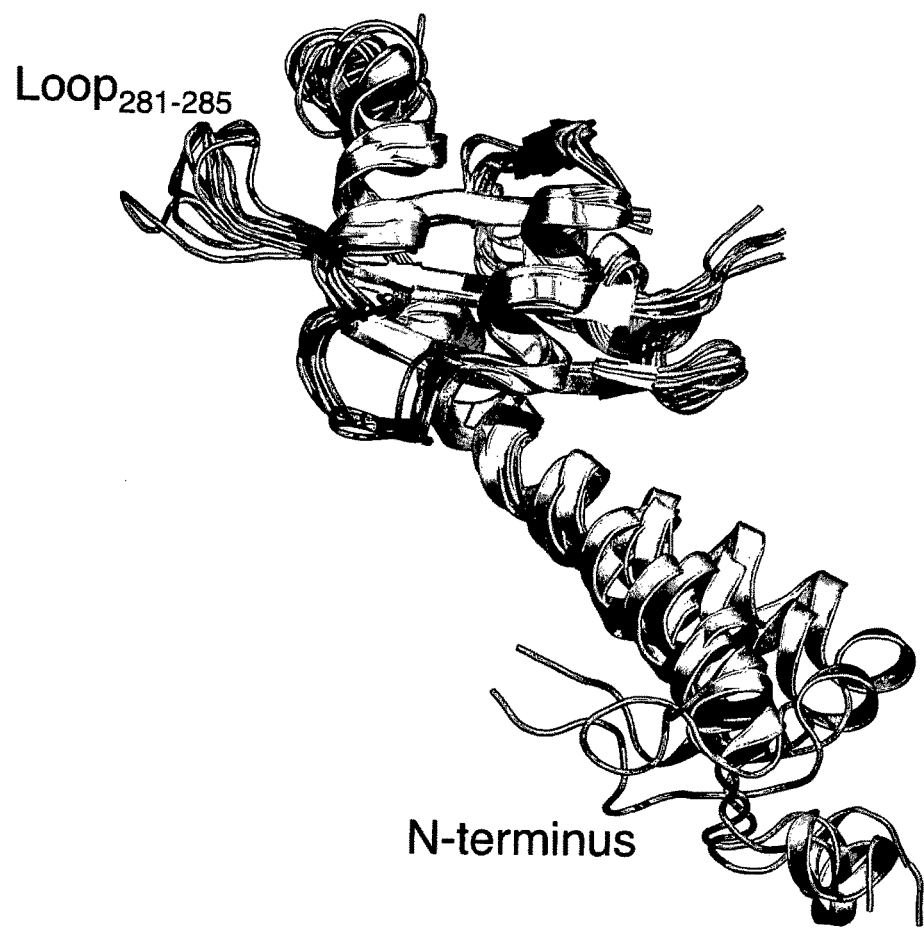
Figure 5E:
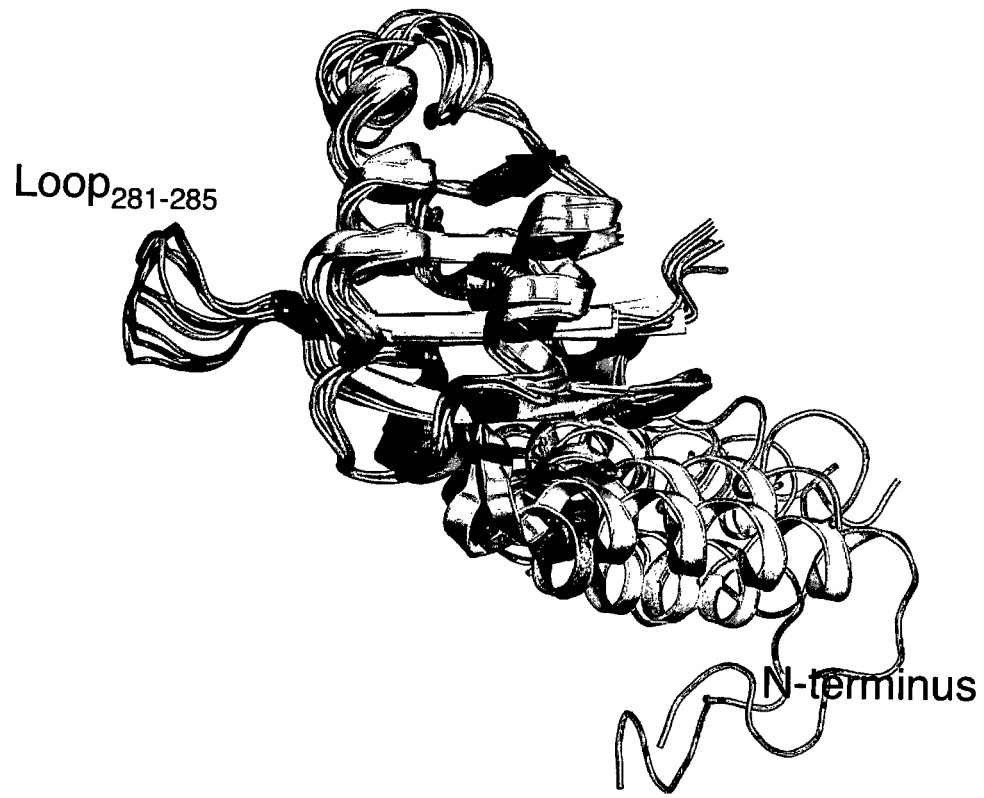

Example 4: Effect of the Mutations of Residues 281-285 of *Salmonella* FlhB on TTSS Function Two strands β2 and β3 were connected by a long flexible loop. This loop was not conserved within the FlhB family, although it is flanked by highly conserved residues, Tyr279 and Pro287 (in *Salmonella* numeration). The length of the loop, which was longer than necessary just for connecting two β-strands, made us to think that it might be of functional importance. To investigate this hypothesis three mutants of *Salmonella* FlhB were created. In the first mutant the loop residues 281-285 were deleted (FIG. 4a). In the second and third mutants residues 281-285 were substituted by Ala or Pro residues, respectively. Then swarming assays on soft agar plates were carried out to investigate whether the *Salmonella* cells, containing mutated FlhB, were still motile. It was observed that deletion of the loop completely abolished motility (FIG. 4b). At the same time substitution by Ala residues had no effect on motility, and Pro substitution decreased motility. To check whether these changes in motility were because of changes in export activity, secretion of hookprotein FlgE and filament protein FliC was analyzed by the flagellar secretion system containing mutated FlhB (FIG. 4c). It was observed that motility is correlated to the secretion of FlgE and FliC. In the case where the loop (281-285) of FlhB is deleted neither FlgE nor FliC were secreted, whereas proline substitution reduced secretion of both proteins. No difference in secretion was observed for the wild-type FlhB and the Ala substitution.

Example 5: Molecular Dynamic Simulation

To further investigate the effect of the loop mutation on the FlhBc molecule, MD simulation of the wild-type Sal FlhB$_C$ and the Δ(281-285), AAAAA$_{281-285}$ (SEQ ID NO: 8), and PPPPP$_{281-285}$ (SEQ ID NO: 9) mutants was performed. During the MD, it was observed that the globular domain was relatively rigid in all the cases, while the N-terminal α-helix of the wild-type FlhB$_C$ was very flexible and becomes less flexible in the mutants (FIG. 5b-e). In addition to the kink around Gly236-Pro238 (FIG. 2a), a significant kink was observed near Met256 during the MD. To characterize the flexibility of the N-terminal α-helix, a distance D, angles θ12, θ23, θ34, θ14 and torsion angles χ3 and χ5 were defined (see explanations in FIG. 5a and Table 2 (SEQ ID NOS: 8 and 9)).

TABLE 2

Structure and fluctuation differences between wild-type *Salmonella* FlhB$_C$ and its mutants during MD simulation shown by key distance and angles defined by vectors V1-5 shown in FIG. 4a, D: length of V5. θ$_{12}$, θ$_{23}$, θ$_{34}$ and θ$_{14}$: angles defined between V1 and V2, V2 and V3, V3 and V4, and V1 and V4, respectively. χ$_3$ and χ$_5$: torsion angles defined by sets of three vectors V2-V3-V4 (torsion around V3) and V1-V5-V4 (around V5), respectively. Averages and standard deviations over last 20 ns MD are shown, with negative values in boldface.

| Protein | D, Å | θ$_{12}$,° | θ$_{23}$,° | θ$_{34}$,° | θ$_{14}$,° | χ$_3$,° | χ$_5$,° |
|---|---|---|---|---|---|---|---|
| *Salmonella* FlhB$_C$ wt | 37.2 ± 3.9 | 96.0 ± 21.9 | 53.8 ± 19.4 | 105.5 ± 2.2 | 77.1 ± 38.3 | 83.8 ± 23.5 | −103.8 ± 44.8 |
| *Salmonella* FlhB$_C$ Δ(281-285) | 36.9 ± 0.7 | 133.2 ± 11.7 | 64.1 ± 5.2 | 108.2 ± 1.7 | 34.0 ± 9.5 | −23.1 ± 7.9 | 168.3 ± 21.0 |
| *Salmonella* FlhB$_C$ AAAAA$_{281-285}$ | 38.1 ± 1.5 | 113.3 ± 34.6 | 45.7 ± 6.1 | 113.2 ± 1.8 | 47.9 ± 35.4 | 30.3 ± 11.6 | −175.5 ± 43.6 |
| *Salmonella* FlhB$_C$ PPPPP$_{281-285}$ | 36.6 ± 3.1 | 69.6 ± 37.1 | 91.4 ± 12.2 | 112.9 ± 2.4 | 59.2 ± 26.9 | −77.3 ± 18.9 | −165.4 ± 43.1 |

A notable structural difference was demonstrated by torsion angle χ3, which determined the direction of the V2 region of the N-terminal α-helix relative to the globular domain. The χ3 value was positive for the wild-type FlhB$_C$ and AAAAA$_{281-285}$ (SEQ ID NO: 8) mutant but negative for the Δ(281-285) and PPPPP$_{281-285}$ (SEQ ID NO: 9) mutants, which was consistent with the structural difference shown in FIG. 5b-e. Since the latter mutations reduced *Salmonella* motility, this structure change might have some functional effects. Another notable difference was seen as reduction in θ12, θ23, θ14, χ3 and χ5 fluctuations in the PPPPP$_{281-285}$ (SEQ ID NO: 9) mutant, indicating the significant structure change and flexibility loss of the N-terminal α-helix.

Example 6: In Silico Screening of Candidate Compounds Interacting with Loop Region of FlhB$_C$ from *Salmonella typhimurium*

Candidate compounds interacting with FlhBc were screened in silico by using Fragment Based Lead Discovery (FBLD) method (provided by PharmaDesign Inc., Japan). This method analyzes in silico the interaction between target protein and moieties of known chemical compound (herein after called as Scaffold).

6.1 Construction of Scaffold Database (Scaffold DB)

Information of Scaffold was generated by following procedure. First, 345,099 of commercially available chemical compounds (dealed by KISHIDA CHEMICAL Co., Ltd.) were selected in view of drug-like, structure to avoid, and molecular weight. Second, ligand information of Protein Data Bank (PDB) was obtained from Ligand Expo (world wide web at ligand-exp.rcsb.org/) which organizes ligand information of PDB. Then, LIGPLOT interaction analysis (world wide web at eb.ac.uk/thornton-srv/software/LIGPLOT/) was performed to obtain hydrogen bond information between atoms of main/side chain of proteins and atoms of ligand, as protein-ligand interaction information. Using the information of the above commercially available chemical compounds as query and protein-ligand interaction information as database, OEChem TK (provided by OpenEye: world wide web at eyesopen.com/oechem-tk/), which can screen substructure, was performed to obtain information of candidate compounds which can mimic the substructure of ligands. Then, Small Molecule Subgraph Detector (SMSD: world wide web at ebi.ac.uk/thornton-srv/software/SMSD/) was used to perform superposing the information of candidate compound to PDB ligand. 889 compounds were finally extracted as Scaffold DB by comparing and examining the result of SMSD and the result of the above protein-ligand interaction information.

6.2 Determination of Scaffold which Recognize Amino Acids Around Loop Region Using Structural Information of FlhB$_C$ Among the amino acid sequence ENKMS (SEQ ID NO: 7) of loop region of FlhB$_C$ from Salmonella typhimurium, residues of ENKS (SEQ ID NO: 10) were involved in hydrogen bond. Thus, the compounds which bond with these ENKS (SEQ ID NO: 10) residues by hydrogen bonding were selected from Scaffold DB. The selected compounds were ranked in view of partition coefficient and solubility calculated by StarDrop (provided by Optibrium: http://www.optibrium.com/stardrop/).

Further, since amino acid sequence PEKDK (SEQ ID NO: 11) of loop region of Aqu FlhB$_C$ aeolicus includes the Asparagine residue which was oriented toward the inward side of the loop in the structural information of Aqu FlhB$_C$, the compounds which bond with Asparagine residues by hydrogen bonding were also selected from Scaffold DB. The selected compounds were ranked by docking simulation using ASEDock of MOE (provided by Chemical Computing Group: http://www.optibrium.com/stardrop/).

As a result, 237 compounds were finally selected.

Example 7: Validation of Inhibitory Activity of Screened Compounds

To evaluate the inhibitory activity of the above selected compounds on secretion of toxin, following assays were performed as described previously (Non-Patent Literature 22).

7.1. Bacterial Growth Assay

Figure 6:
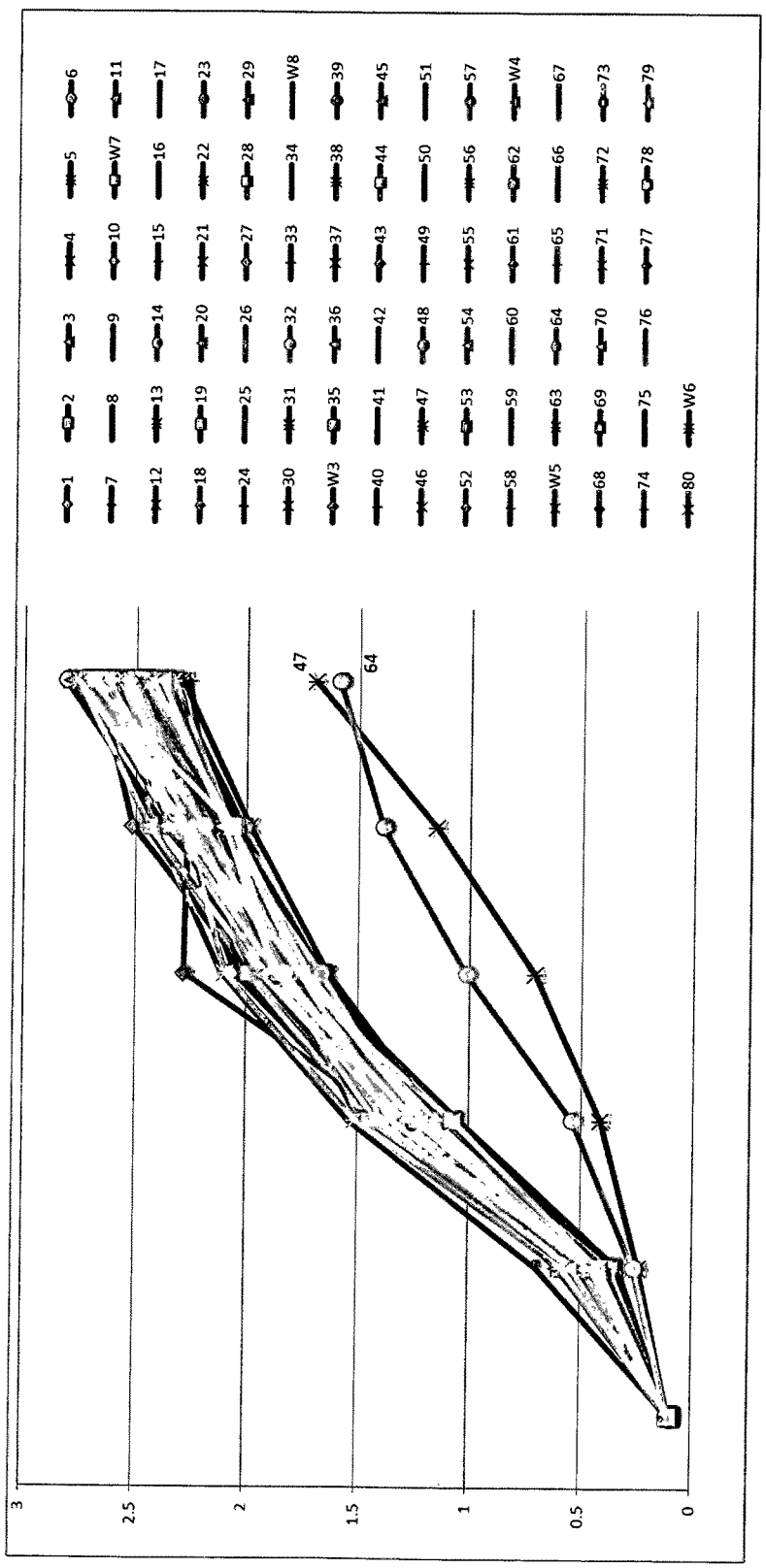
FIG. 6: Bacterial growth in presence of candidate compounds. The ordinate shows the optical density at 600 nm (OD 600). The abscissa shows the measured time points (2, 4, 6, 8 and 10 hours).

The effect of the candidate compounds on the viability of bacteria cultures were first tested before analyzing their effect on the flexibility of FlhB$_C$. 80 compounds out of the 237 compounds were purchased from KISHIDA CHEMICAL Co., Ltd according to the ranking. The Salmonella typhimurium strain SJW1103 was grown in LB medium at 303 K. Overnight cultures were diluted in Fresh LB medium to an optical density at 600 nm (OD600) of 0.1. Each of 5 µl of 100 mM candidate compounds solubilized in DMSO or DMSO alone as a control was added into 10 ml LB medium in 50-ml volume polypropylene conical tubes. For obtaining growth curves of the cell under the presence of each chemical, 0.2 ml of the culture volume were removed at every 2 h (2, 4, 6, 8 and 10 hr) and diluted with 1 ml of LB to measure absorbance at OD600. As a result, all 80 compounds did not lead to severe growth defects (FIG. 6). 2 compounds (compound 47 and compound 64) showed slight growth delay, but that slight delay was considered as not influential for the subsequent experiment.

7.2. Secretion Assay

Then, effects of the selected compounds on different type III secretion phenotypes were assessed. 1 ml of the cell suspensions of 8.0 hr culture in the above-growth assay were centrifuged at 13,200 rpm (16,100 g) for 10 min. The supernatant fractions (0.9 ml) were fractionated into new tubes and mixed with 100% trichloroacetic acid thoroughly. The fractions were kept on ice at least 1 h to precipitate secreted proteins. After centrifugation at 15,400 rpm for 30 min, the precipitated supernatant fractions were resuspended in 0.02 ml of 1 M Tris base and stored −30° C. until use. Samples for SDS-PAGE analysis were prepared by adding 5× SDS loading Buffer and then heat at 95° C. for 5 min. SDS-PAGE analyses were carried out at the condition of 200V for 30 min using premade gels purchased from Bio-rad. Electro-blotting onto PVDF membrane was performed with iBlot from Invitrogen and the membranes were developed with Chromogenic Immuno-detection Kit (Invitrogen) using a custom antibody raised against FlgD, a flagellar protein (from Prof. Keiichi Namba, Osaka University). Images were digitized as gray scale color with ChemDoc (Bio-rad). Kaleidoscope (Bio-rad) was used as a molecular marker.

Figure 7A:
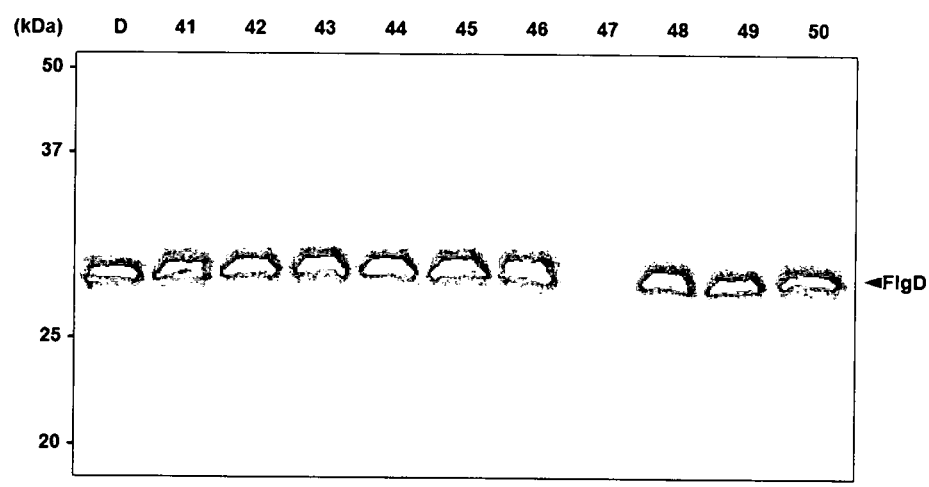
FIG. 7: Inhibitory effect of screened compounds on FlgD secretion. (a) and (b) Western blots of suspension of *Salmonella typhimurium* strain SJW1103 incubated 8 hours with screened compounds.
Figure 7B:
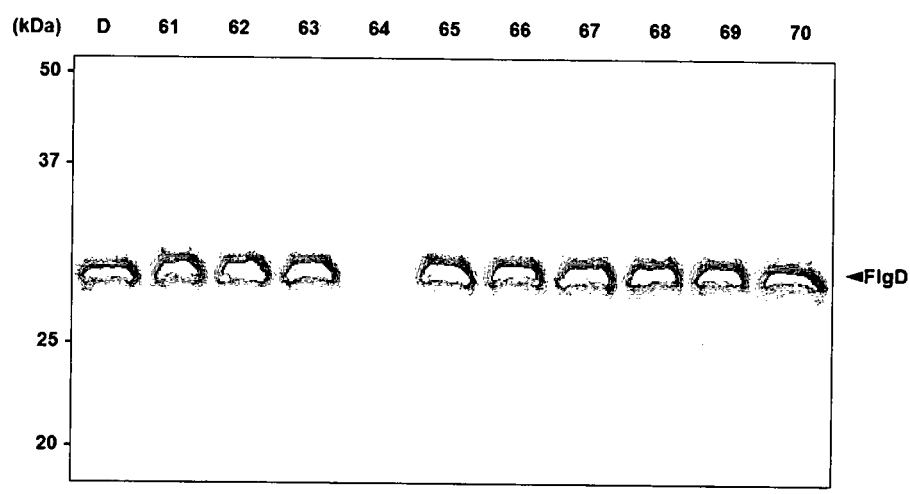

As a result, 7-(2,3-dihydroxypropyl)-1,3-dimethyl-3,7-dihydro-1H-purine-2,6-dione (compound 47: also known as dyphylline) and 5-(3,4,5-Trimethoxybenzyl)pyrimidine-2,4-diamine (compound 64: also known as Trimethoprim) were demonstrated to inhibit the secretion of FlgD, which is typical protein secreted by TTSS (Non-Patent Literature 11 and Non-Patent Literature 13) (FIG. 7a and FIG. 7b). This inhibitory activity of the compounds suggested the effects of compounds on inhibition of flexibility of FlhB$_C$.

What is claimed is:

1. A method for screening a compound that inhibits secretion of toxins into the host-cell cytoplasm by virulent bacteria using a needle type III secretion system, wherein the toxins are secreted by the needle type III secretion system and wherein the virulent bacteria is *Salmonella typhimurium*, the method comprising the steps of:

contacting a candidate compound with a C-terminal cytoplasmic domain of the membrane protein FlhB (SEQ ID NO: 1) from *Salmonella typhimurium* or an amino acid sequence variant that is at least 90% identical to SEQ ID NO: 1, analyzing the interaction of the candidate compound with a loop region consisting of amino acids Glu, Asn, Lys, Met and Ser at positions 281 to 285 of FlhB (SEQ ID NO:1) or with the loop region of said variant that is at least 90% identical to SEQ ID NO: 1, wherein the loop region of said variant consists of amino acids Glu, Asn, Lys, Met and Ser, which correspond to positions 281 to 285 of FlhB (SEQ ID NO: 1), and selecting a compound that reduces the flexibility of the loop region of FlhB or the amino acid sequence variant.

2. The method of claim 1, wherein the interaction of the compound with the loop region of the cytoplasmic domain of FlhB or the amino acid sequence variant is determined by whether or not the compound differentially binds to the membrane protein FlhB from *Salmonella typhimurium* and its Δ(281-285) mutant protein.

3. The method of claim 1, wherein the compound that inhibits the secretion of toxins by virulent bacteria is an antibody or a fragment thereof, an aptamer or a small molecular compound.

4. A method for screening a compound that inhibits secretion of toxins into the host-cell cytoplasm by virulent bacteria using a needle type III secretion system, wherein the toxins are secreted by the needle type III secretion system and wherein the virulent bacteria is *Salmonella typhimurium*, the method comprising the steps of:

i) selecting a set of candidate compounds capable of interacting with a membrane protein FlhB (SEQ ID NO: 1) or an amino acid sequence variant that is at least 90% identical to SEQ ID NO: 1 from *Salmonella typhimurium*, by a hydrogen bond between at least one side chain of a loop region consisting of Glu, Asn, Lys, Met and Ser at positions 281 to 285 of FlhB (SEQ ID NO:1) or with the loop region of said variant that is at least 90% identical to SEQ ID NO: 1, wherein the loop region of said variant consists of amino acids Glu, Asn, Lys, Met and Ser, which correspond to positions 281 to 285 of FlhB (SEQ ID NO: 1), and the candidate compound, ii) contacting the candidate compounds with bacteria having a flagellar and needle type III secretion system, and iii) selecting a compound from the set of candidate compounds that reduces secretion of proteins secreted by the type III secretion system from the bacteria and/or motility of the bacteria using a flagellum.

* * * * *

SEQUENCE LISTING

<160> NUMBER OF SEQ ID NOS: 11

<210> SEQ ID NO 1
<211> LENGTH: 383
<212> TYPE: PRT
<213> ORGANISM: Salmonella typhimurium

<400> SEQUENCE: 1

Met Ala Glu Glu Ser Asp Asp Lys Thr Glu Ala Pro Thr Pro His
1               5                   10                  15

Arg Leu Glu Lys Ala Arg Glu Glu Gly Gln Ile Pro Arg Ser Arg Glu
                20                  25                  30

Leu Thr Ser Leu Leu Ile Leu Leu Val Gly Val Cys Ile Ile Trp Phe
            35                  40                  45

Gly Gly Glu Ser Leu Ala Arg Gln Leu Ala Gly Met Leu Ser Ala Gly
        50                  55                  60

```
Leu His Phe Asp His Arg Met Val Asn Asp Pro Asn Leu Ile Leu Gly
 65                  70                  75                  80

Gln Ile Ile Leu Leu Ile Lys Ala Ala Met Met Ala Leu Leu Pro Leu
                 85                  90                  95

Ile Ala Gly Val Val Leu Val Ala Leu Ile Ser Pro Val Met Leu Gly
            100                 105                 110

Gly Leu Ile Phe Ser Gly Lys Ser Leu Gln Pro Lys Phe Ser Lys Leu
            115                 120                 125

Asn Pro Leu Pro Gly Ile Lys Arg Met Phe Ser Ala Gln Thr Gly Ala
            130                 135                 140

Glu Leu Leu Lys Ala Val Leu Lys Ser Thr Leu Val Gly Cys Val Thr
145                 150                 155                 160

Gly Phe Tyr Leu Trp His His Trp Pro Gln Met Met Arg Leu Met Ala
                165                 170                 175

Glu Ser Pro Ile Val Ala Met Gly Asn Ala Leu Asp Leu Val Gly Leu
            180                 185                 190

Cys Ala Leu Leu Val Leu Gly Val Ile Pro Met Val Gly Phe Asp
            195                 200                 205

Val Phe Phe Gln Ile Phe Ser His Leu Lys Lys Leu Arg Met Ser Arg
210                 215                 220

Gln Asp Ile Arg Asp Glu Phe Lys Glu Ser Glu Gly Asp Pro His Val
225                 230                 235                 240

Lys Gly Lys Ile Arg Gln Met Gln Arg Ala Ala Gln Arg Met
            245                 250                 255

Met Glu Asp Val Pro Lys Ala Asp Val Ile Val Thr Asn Pro Thr His
            260                 265                 270

Tyr Ser Val Ala Leu Gln Tyr Asp Glu Asn Lys Met Ser Ala Pro Lys
            275                 280                 285

Val Val Ala Lys Gly Ala Gly Leu Ile Ala Leu Arg Ile Arg Glu Ile
290                 295                 300

Gly Ala Glu His Arg Val Pro Thr Leu Glu Ala Pro Pro Leu Ala Arg
305                 310                 315                 320

Ala Leu Tyr Arg His Ala Glu Ile Gly Gln Gln Ile Pro Gly Gln Leu
                325                 330                 335

Tyr Ala Ala Val Ala Glu Val Leu Ala Trp Val Trp Gln Leu Lys Arg
            340                 345                 350

Trp Arg Leu Ala Gly Gly Gln Arg Pro Pro Gln Pro Glu Asn Leu Pro
                355                 360                 365

Val Pro Glu Ala Leu Asp Phe Met Asn Glu Lys Asn Thr Asp Gly
            370                 375                 380

<210> SEQ ID NO 2
<211> LENGTH: 350
<212> TYPE: PRT
<213> ORGANISM: Aquifex aeolicus

<400> SEQUENCE: 2

Met Ala Glu Glu His Lys Thr Glu Arg Ala Thr Pro Tyr Lys Arg Arg
 1               5                  10                  15

Lys Val Arg Glu Glu Gly Asn Val Ala Lys Ser His Glu Ile Ala Ser
                20                  25                  30

Ser Leu Val Val Leu Leu Ser Leu Leu Leu Leu Phe Leu Gly Thr
            35                  40                  45

Tyr Ile Ala Lys Glu Val Ile Leu Ile Phe Leu Ala Val Thr Gly Tyr
```

```
            50                  55                  60
Val His Ala Asp Ile Ser Glu Leu Gly Ser Leu Tyr Glu Asn Phe Tyr
 65                  70                  75                  80

Glu Asn Ile Val Lys Val Leu Thr Pro Leu Phe Leu Ala Leu Leu
                 85                  90                  95

Val Val Ile Leu Ser His Val Ala Gln Phe Gly Phe Ile Phe Thr Leu
                100                 105                 110

Lys Pro Leu Ser Phe Lys Trp Glu Arg Ile Asn Pro Phe Glu Gly Ile
            115                 120                 125

Lys Arg Leu Ile Ser Leu Thr Thr Leu Phe Glu Thr Val Lys Asn Thr
            130                 135                 140

Leu Lys Ala Phe Leu Leu Ile Gly Ile Ala Val Phe Val Leu Lys Gly
145                 150                 155                 160

Ser Leu Tyr Phe Phe Leu Ser Ser Ser Thr Tyr Pro Leu Ala Glu Thr
                165                 170                 175

Leu Lys Ser Phe Ile Lys Thr Ser Ala Ile Thr Leu Ile Thr Leu Gly
            180                 185                 190

Val Val Ala Leu Leu Ile Ala Phe Leu Asp Tyr Ala Phe Lys Arg Trp
            195                 200                 205

Gln Tyr Glu Lys Lys Ile Met Met Ser Arg Arg Glu Leu Lys Glu Glu
            210                 215                 220

Tyr Lys Gln Leu Glu Gly His Pro Glu Val Lys Ser Arg Ile Lys Ala
225                 230                 235                 240

Arg Met Arg Glu Leu Ala Lys Ser Arg Met Met Ala Glu Val Pro Lys
                245                 250                 255

Ala Thr Val Val Ile Thr Asn Pro Thr His Ile Ala Ile Ala Leu Lys
            260                 265                 270

Tyr Asn Pro Glu Lys Asp Lys Ala Pro Val Val Ala Lys Gly Lys
            275                 280                 285

Gly Thr Ile Ala Gln Lys Ile Val Glu Ile Ala Glu Asn Tyr Ser Ile
            290                 295                 300

Pro Val Val Arg Lys Pro Glu Leu Ala Arg Ala Leu Tyr Pro Ala Val
305                 310                 315                 320

Glu Val Gly Lys Glu Ile Ser Pro Lys Phe Tyr Lys Ala Val Ala Glu
                325                 330                 335

Ile Ile Ala Tyr Val Met Phe Lys Lys Lys Val Tyr Ala
            340                 345                 350

<210> SEQ ID NO 3
<211> LENGTH: 345
<212> TYPE: PRT
<213> ORGANISM: Escherichia coli

<400> SEQUENCE: 3

Met Ser Glu Lys Thr Glu Lys Pro Thr Pro Lys Lys Leu Arg Asp Leu
 1               5                  10                  15

Lys Lys Lys Gly Asp Val Thr Lys Ser Glu Val Met Ala Ala Val
                 20                  25                  30

Gln Ser Leu Ile Leu Phe Ser Phe Ser Leu Tyr Gly Met Ser Phe
                 35                  40                  45

Phe Val Asp Ile Val Gly Leu Val Asn Thr Thr Ile Asp Ser Leu Asn
             50                  55                  60

Arg Pro Phe Leu Tyr Ala Ile Arg Glu Ile Leu Gly Ala Val Leu Asn
 65                  70                  75                  80
```

Ile Phe Leu Leu Tyr Ile Leu Pro Ile Ser Leu Ile Val Phe Val Gly
                85                  90                  95

Thr Val Thr Thr Gly Val Ser Gln Ile Gly Phe Ile Phe Ala Val Glu
            100                 105                 110

Lys Ile Lys Pro Ser Ala Gln Lys Ile Ser Val Lys Asn Asn Leu Lys
        115                 120                 125

Asn Ile Phe Ser Val Lys Ser Ile Phe Glu Leu Leu Lys Ser Val Phe
    130                 135                 140

Lys Leu Val Ile Ile Val Leu Ile Phe Tyr Phe Met Gly His Ser Tyr
145                 150                 155                 160

Ala Asn Glu Phe Ala Asn Phe Thr Gly Leu Asn Ala Tyr Gln Ala Leu
                165                 170                 175

Val Val Val Ala Phe Phe Val Phe Leu Leu Trp Lys Gly Val Leu Phe
            180                 185                 190

Gly Tyr Leu Leu Phe Ser Val Phe Asp Phe Trp Phe Gln Lys His Glu
        195                 200                 205

Gly Leu Lys Lys Met Lys Met Ser Lys Asp Glu Val Lys Arg Glu Ala
    210                 215                 220

Lys Asp Thr Asp Gly Asn Pro Glu Ile Lys Gly Glu Arg Arg Leu
225                 230                 235                 240

His Ser Glu Ile Gln Ser Gly Ser Leu Ala Asn Asn Ile Lys Lys Ser
                245                 250                 255

Thr Val Ile Val Lys Asn Pro Thr His Ile Ala Ile Cys Leu Tyr Tyr
            260                 265                 270

Lys Leu Gly Glu Thr Pro Leu Pro Leu Val Ile Glu Thr Gly Lys Asp
        275                 280                 285

Ala Lys Ala Leu Gln Ile Ile Lys Leu Ala Glu Leu Tyr Asp Ile Pro
    290                 295                 300

Val Ile Glu Asp Ile Pro Leu Ala Arg Thr Leu Tyr Lys Asn Ile His
305                 310                 315                 320

Lys Gly Gln Tyr Ile Thr Glu Asp Phe Phe Gly Pro Val Ala Gln Leu
                325                 330                 335

Ile Arg Ile Ala Ile Asp Leu Asp Tyr
            340                 345

<210> SEQ ID NO 4
<211> LENGTH: 354
<212> TYPE: PRT
<213> ORGANISM: Yersinia pestis

<400> SEQUENCE: 4

Met Ser Gly Glu Lys Thr Glu Gln Pro Thr Pro Lys Lys Ile Arg Asp
1               5                   10                  15

Ala Arg Lys Lys Gly Gln Val Ala Ser Lys Glu Val Val Ser Thr
            20                  25                  30

Ala Leu Ile Val Ala Leu Ser Ala Met Leu Met Gly Leu Ser Asp Tyr
        35                  40                  45

Tyr Phe Glu His Phe Ser Lys Leu Met Leu Ile Pro Ala Glu Gln Ser
    50                  55                  60

Tyr Leu Pro Phe Ser Gln Ala Leu Ser Tyr Val Val Asp Asn Val Leu
65                  70                  75                  80

Leu Glu Phe Phe Tyr Leu Cys Phe Pro Leu Leu Thr Val Ala Ala Leu
                85                  90                  95

Met Ala Ile Ala Ser His Val Val Gln Tyr Gly Phe Leu Ile Ser Gly
            100                 105                 110

Glu Ala Ile Lys Pro Asp Ile Lys Lys Ile Asn Pro Ile Glu Gly Ala
            115                 120                 125

Lys Arg Ile Phe Ser Ile Lys Ser Leu Val Glu Phe Leu Lys Ser Ile
        130                 135                 140

Leu Lys Val Val Leu Leu Ser Ile Leu Ile Trp Ile Ile Ile Lys Gly
145                 150                 155                 160

Asn Leu Val Thr Leu Leu Gln Leu Pro Thr Cys Gly Ile Glu Cys Ile
                165                 170                 175

Thr Pro Leu Leu Gly Gln Ile Leu Arg Gln Leu Met Val Ile Cys Thr
            180                 185                 190

Val Gly Phe Val Val Ile Ser Ile Ala Asp Tyr Ala Phe Glu Tyr Tyr
        195                 200                 205

Gln Tyr Ile Lys Glu Leu Lys Met Ser Lys Asp Glu Ile Lys Arg Glu
    210                 215                 220

Tyr Lys Glu Met Glu Gly Ser Pro Glu Ile Lys Ser Lys Arg Arg Gln
225                 230                 235                 240

Phe His Gln Glu Ile Gln Ser Arg Asn Met Arg Glu Asn Val Lys Arg
                245                 250                 255

Ser Ser Val Val Val Ala Asn Pro Thr His Ile Ala Ile Gly Ile Leu
            260                 265                 270

Tyr Lys Arg Gly Glu Thr Pro Leu Pro Leu Val Thr Phe Lys Tyr Thr
        275                 280                 285

Asp Ala Gln Val Gln Thr Val Arg Lys Ile Ala Glu Glu Gly Val
    290                 295                 300

Pro Ile Leu Gln Arg Ile Pro Leu Ala Arg Ala Leu Tyr Trp Asp Ala
305                 310                 315                 320

Leu Val Asp His Tyr Ile Pro Ala Glu Gln Ile Glu Ala Thr Ala Glu
                325                 330                 335

Val Leu Arg Trp Leu Glu Arg Gln Asn Ile Glu Lys Gln His Ser Glu
            340                 345                 350

Met Leu

<210> SEQ ID NO 5
<211> LENGTH: 356
<212> TYPE: PRT
<213> ORGANISM: Salmonella typhimurium

<400> SEQUENCE: 5

Met Ser Ser Asn Lys Thr Glu Lys Pro Thr Lys Lys Arg Leu Glu Asp
1               5                   10                  15

Ser Ala Lys Lys Gly Gln Ser Phe Lys Ser Lys Asp Leu Ile Ile Ala
            20                  25                  30

Cys Leu Thr Leu Gly Gly Ile Ala Tyr Leu Val Ser Tyr Gly Ser Phe
        35                  40                  45

Asn Glu Phe Met Gly Ile Ile Lys Ile Ile Ala Asp Asn Phe Asp
    50                  55                  60

Gln Ser Met Ala Asp Tyr Ser Leu Ala Val Phe Gly Ile Gly Leu Lys
65                  70                  75                  80

Tyr Leu Ile Pro Phe Met Leu Cys Leu Val Cys Ser Ala Leu Pro
                85                  90                  95

Ala Leu Leu Gln Ala Gly Phe Val Leu Ala Thr Glu Ala Leu Lys Pro
            100                 105                 110

Asn Leu Ser Ala Leu Asn Pro Val Glu Gly Ala Lys Lys Leu Phe Ser
        115                 120                 125

Met Arg Thr Val Lys Asp Thr Val Lys Thr Leu Leu Tyr Leu Ser Ser
130                 135                 140

Phe Val Val Ala Ala Ile Ile Cys Trp Lys Lys Tyr Lys Val Glu Ile
145                 150                 155                 160

Phe Ser Gln Leu Asn Gly Asn Ile Val Gly Ile Ala Val Ile Trp Arg
                165                 170                 175

Glu Leu Leu Leu Ala Leu Val Leu Thr Cys Leu Ala Cys Ala Leu Ile
                180                 185                 190

Val Leu Leu Leu Asp Ala Ile Ala Glu Tyr Phe Leu Thr Met Lys Asp
                195                 200                 205

Met Lys Met Asp Lys Glu Glu Val Lys Arg Glu Met Lys Glu Gln Glu
210                 215                 220

Gly Asn Pro Glu Val Lys Ser Lys Arg Arg Glu Val His Met Glu Ile
225                 230                 235                 240

Leu Ser Glu Gln Val Lys Ser Asp Ile Glu Asn Ser Arg Leu Ile Val
                245                 250                 255

Ala Asn Pro Thr His Ile Thr Ile Gly Ile Tyr Phe Lys Pro Glu Leu
                260                 265                 270

Met Pro Ile Pro Met Ile Ser Val Tyr Glu Thr Asn Gln Arg Ala Leu
                275                 280                 285

Ala Val Arg Ala Tyr Ala Glu Lys Val Gly Val Pro Val Ile Val Asp
                290                 295                 300

Ile Lys Leu Ala Arg Ser Leu Phe Lys Thr His Arg Arg Tyr Asp Leu
305                 310                 315                 320

Val Ser Leu Glu Glu Ile Asp Glu Val Leu Arg Leu Leu Val Trp Leu
                325                 330                 335

Glu Glu Val Glu Asn Ala Gly Lys Asp Val Ile Gln Pro Gln Glu Asn
                340                 345                 350

Glu Val Arg His
            355

<210> SEQ ID NO 6
<211> LENGTH: 342
<212> TYPE: PRT
<213> ORGANISM: Shigella flexneri

<400> SEQUENCE: 6

Met Ala Asn Lys Thr Glu Lys Pro Thr Pro Lys Lys Leu Lys Asp Ala
1               5                   10                  15

Ala Lys Lys Gly Gln Ser Phe Lys Phe Lys Asp Leu Thr Thr Val Val
                20                  25                  30

Ile Ile Leu Val Gly Thr Phe Thr Ile Ile Ser Phe Phe Ser Leu Ser
                35                  40                  45

Asp Val Met Leu Leu Tyr Arg Tyr Val Ile Ile Asn Asp Phe Glu Ile
50                  55                  60

Asn Glu Gly Lys Tyr Phe Phe Ala Val Val Ile Val Phe Phe Lys Ile
65                  70                  75                  80

Ile Gly Phe Pro Leu Phe Phe Cys Val Leu Ser Ala Val Leu Pro Thr
                85                  90                  95

Leu Val Gln Thr Lys Phe Val Leu Ala Thr Lys Ala Ile Lys Ile Asp
                100                 105                 110

Phe Ser Val Leu Asn Pro Val Lys Gly Leu Lys Ile Phe Ser Ile
                115                 120                 125

Lys Thr Ile Lys Glu Phe Phe Lys Ser Ile Leu Leu Leu Ile Ile Leu

```
                130             135             140
Ala Leu Thr Thr Tyr Phe Phe Trp Ile Asn Asp Arg Lys Ile Ile Phe
145                 150                 155                 160

Ser Gln Val Phe Ser Ser Val Asp Gly Leu Tyr Leu Ile Trp Gly Gly
                165                 170                 175

Leu Phe Lys Asp Ile Ile Leu Phe Phe Leu Ala Phe Ser Ile Phe Val
            180                 185                 190

Ile Ile Leu Asp Phe Val Ile Glu Phe Ile Leu Tyr Met Lys Asp Met
        195                 200                 205

Met Met Asp Lys Gln Glu Ile Lys Arg Glu Tyr Ile Glu Gln Glu Gly
        210                 215                 220

His Phe Glu Thr Lys Ser Arg Arg Glu Leu His Ile Glu Ile Leu
225                 230                 235                 240

Ser Glu Gln Thr Lys Ser Asp Ile Arg Asn Ser Lys Leu Val Val Met
                245                 250                 255

Asn Pro Thr His Ile Ala Ile Gly Ile Tyr Phe Asn Pro Glu Ile Ala
                260                 265                 270

Pro Ala Pro Phe Ile Ser Leu Ile Glu Thr Asn Gln Cys Ala Leu Ala
            275                 280                 285

Val Arg Lys Tyr Ala Asn Glu Val Gly Ile Pro Thr Val Arg Asp Val
        290                 295                 300

Lys Leu Ala Arg Lys Leu Tyr Lys Thr His Thr Lys Tyr Ser Phe Val
305                 310                 315                 320

Asp Phe Glu His Leu Asp Glu Val Leu Arg Leu Ile Val Trp Leu Glu
                325                 330                 335

Gln Val Glu Asn Thr His
            340

<210> SEQ ID NO 7
<211> LENGTH: 5
<212> TYPE: PRT
<213> ORGANISM: Salmonella typhimurium

<400> SEQUENCE: 7

Glu Asn Lys Met Ser
1               5

<210> SEQ ID NO 8
<211> LENGTH: 5
<212> TYPE: PRT
<213> ORGANISM: Salmonella typhimurium

<400> SEQUENCE: 8

Ala Ala Ala Ala Ala
1               5

<210> SEQ ID NO 9
<211> LENGTH: 5
<212> TYPE: PRT
<213> ORGANISM: Salmonella typhimurium

<400> SEQUENCE: 9

Pro Pro Pro Pro Pro
1               5

<210> SEQ ID NO 10
<211> LENGTH: 4
<212> TYPE: PRT
<213> ORGANISM: Salmonella typhimurium
```

```
<400> SEQUENCE: 10

Glu Asn Lys Ser
1

<210> SEQ ID NO 11
<211> LENGTH: 5
<212> TYPE: PRT
<213> ORGANISM: Aquifex aeolicus

<400> SEQUENCE: 11

Pro Glu Lys Asp Lys
1               5
```